(12) United States Patent
Pathak

(10) Patent No.: US 7,785,512 B1
(45) Date of Patent: Aug. 31, 2010

(54) METHOD AND SYSTEM OF CONTROLLED TEMPERATURE MIXING AND MOLDING OF POLYMERS WITH ACTIVE AGENTS FOR IMPLANTABLE MEDICAL DEVICES

(75) Inventor: Jaya Pathak, Carlsbad, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 1355 days.

(21) Appl. No.: 10/853,924

(22) Filed: May 25, 2004

Related U.S. Application Data

(63) Continuation-in-part of application No. 10/631,228, filed on Jul. 31, 2003, now Pat. No. 7,645,474.

(51) Int. Cl.
*B29C 47/92* (2006.01)
(52) U.S. Cl. .................... 264/211; 264/40.6
(58) Field of Classification Search ........................ None
See application file for complete search history.

(56) References Cited

U.S. PATENT DOCUMENTS

| | | | |
|---|---|---|---|
| 2,072,303 A | 3/1937 | Herrmann et al. | 128/335.5 |
| 2,386,454 A | 10/1945 | Frosch et al. | 260/78 |
| 3,773,737 A | 11/1973 | Goodman et al. | 260/78 |
| 3,849,514 A | 11/1974 | Gray, Jr. et al. | 260/857 |
| 4,117,714 A | 10/1978 | Goodson et al. | |
| 4,226,243 A | 10/1980 | Shalaby et al. | 128/335.5 |
| 4,329,383 A | 5/1982 | Joh | 428/36 |
| 4,343,931 A | 8/1982 | Barrows | 528/291 |
| 4,384,072 A | 5/1983 | Newman et al. | |
| 4,529,792 A | 7/1985 | Barrows | 528/291 |
| 4,611,051 A | 9/1986 | Hayes et al. | 528/295.3 |
| 4,656,242 A | 4/1987 | Swan et al. | 528/295.3 |
| 4,733,665 A | 3/1988 | Palmaz | 128/343 |

(Continued)

FOREIGN PATENT DOCUMENTS

DE        42 24 401        1/1994

(Continued)

OTHER PUBLICATIONS

Anonymous, *Cardiologists Draw— Up The Dream Stent*, Clinica 710:15 (Jun. 17, 1996), http://www.dialogweb.com/cgi/document?reg=1061848202959, printed Aug. 25, 2003 (2 pages).

(Continued)

*Primary Examiner*—Monica A Huson
(74) *Attorney, Agent, or Firm*—Squire, Sanders & Dempsey, L.L.P.

(57) ABSTRACT

A method and system for making a composition for use in manufacturing an implantable medical device, such as a drug-eluting and/or delivery stent, is described. The method includes introducing a polymer, active agent, and a solvent into a mixing apparatus such as an extruder. The polymer, active agent, and solvent may be mixed in the apparatus to form a homogeneous or substantially homogeneous polymer mixture. The method may further include controlling a temperature of the polymer mixture in at least a portion of the apparatus. In an embodiment, the polymer mixture may be used as a coating for an implantable medical device, or fabricating an implantable medical device. The invention also includes a composition formed by the method described above.

45 Claims, 3 Drawing Sheets

U.S. PATENT DOCUMENTS

| | | | |
|---|---|---|---|
| 4,800,882 A | 1/1989 | Gianturco | 128/343 |
| 4,882,168 A | 11/1989 | Casey et al. | 424/468 |
| 4,886,062 A | 12/1989 | Wiktor | 128/343 |
| 4,931,287 A | 6/1990 | Bae et al. | 424/484 |
| 4,941,870 A | 7/1990 | Okada et al. | 600/36 |
| 4,977,901 A | 12/1990 | Ofstead | 128/772 |
| 5,019,096 A | 5/1991 | Fox, Jr. et al. | 623/1 |
| 5,100,992 A | 3/1992 | Cohn et al. | 424/501 |
| 5,112,457 A | 5/1992 | Marchant | 204/165 |
| 5,133,742 A | 7/1992 | Pinchuk | 623/1 |
| 5,163,952 A | 11/1992 | Froix | 623/1 |
| 5,165,919 A | 11/1992 | Sasaki et al. | 424/488 |
| 5,183,690 A * | 2/1993 | Carr et al. | 427/213.31 |
| 5,219,980 A | 6/1993 | Swidler | 528/272 |
| 5,258,020 A | 11/1993 | Froix | 623/1 |
| 5,272,012 A | 12/1993 | Opolski | 428/423.1 |
| 5,292,516 A | 3/1994 | Viegas et al. | 424/423 |
| 5,298,260 A | 3/1994 | Viegas et al. | 424/486 |
| 5,300,295 A | 4/1994 | Viegas et al. | 424/427 |
| 5,306,501 A | 4/1994 | Viegas et al. | 424/423 |
| 5,306,786 A | 4/1994 | Moens et al. | 525/437 |
| 5,328,471 A | 7/1994 | Slepian | 604/101 |
| 5,330,768 A | 7/1994 | Park et al. | 424/501 |
| 5,380,299 A | 1/1995 | Fearnot et al. | 604/265 |
| 5,417,981 A | 5/1995 | Endo et al. | 424/486 |
| 5,447,724 A | 9/1995 | Helmus et al. | 424/426 |
| 5,455,040 A | 10/1995 | Marchant | 424/426 |
| 5,462,990 A | 10/1995 | Hubbell et al. | 525/54.1 |
| 5,464,650 A | 11/1995 | Berg et al. | 427/2.3 |
| 5,485,496 A | 1/1996 | Lee et al. | 378/64 |
| 5,516,881 A | 5/1996 | Lee et al. | 528/320 |
| 5,569,463 A | 10/1996 | Helmus et al. | 424/426 |
| 5,578,073 A | 11/1996 | Haimovich et al. | 623/1 |
| 5,584,877 A | 12/1996 | Miyake et al. | 623/1 |
| 5,605,696 A | 2/1997 | Eury et al. | 424/423 |
| 5,607,467 A | 3/1997 | Froix | 623/1 |
| 5,609,629 A | 3/1997 | Fearnot et al. | 623/1 |
| 5,610,241 A | 3/1997 | Lee et al. | 525/411 |
| 5,616,338 A | 4/1997 | Fox, Jr. et al. | 424/423 |
| 5,624,411 A | 4/1997 | Tuch | 604/265 |
| 5,628,730 A | 5/1997 | Shapland et al. | 604/21 |
| 5,644,020 A | 7/1997 | Timmermann et al. | 528/288 |
| 5,649,977 A | 7/1997 | Campbell | 623/1 |
| 5,658,995 A | 8/1997 | Kohn et al. | 525/432 |
| 5,667,767 A | 9/1997 | Greff et al. | 424/9.411 |
| 5,670,558 A | 9/1997 | Onishi et al. | 523/112 |
| 5,674,242 A | 10/1997 | Phan et al. | 606/198 |
| 5,679,400 A | 10/1997 | Tuch | 427/2.14 |
| 5,700,286 A | 12/1997 | Tartaglia et al. | 623/1 |
| 5,702,754 A | 12/1997 | Zhong | 427/2.12 |
| 5,711,958 A | 1/1998 | Cohn et al. | 424/423 |
| 5,716,981 A | 2/1998 | Hunter et al. | 514/449 |
| 5,721,131 A | 2/1998 | Rudolph et al. | 435/240 |
| 5,723,219 A | 3/1998 | Kolluri et al. | 428/411.1 |
| 5,735,897 A | 4/1998 | Buirge | 623/12 |
| 5,746,998 A | 5/1998 | Torchilin et al. | 424/9.4 |
| 5,756,553 A | 5/1998 | Iguchi et al. | |
| 5,756,659 A | 5/1998 | Hughes et al. | |
| 5,759,205 A | 6/1998 | Valentini | 623/16 |
| 5,762,944 A * | 6/1998 | Inoue et al. | 424/400 |
| 5,776,184 A | 7/1998 | Tuch | 623/1 |
| 5,783,657 A | 7/1998 | Pavlin et al. | 528/310 |
| 5,788,979 A | 8/1998 | Alt et al. | 424/426 |
| 5,800,392 A | 9/1998 | Racchini | 604/96 |
| 5,820,917 A | 10/1998 | Tuch | 427/2.1 |
| 5,824,048 A | 10/1998 | Tuch | 623/1 |
| 5,824,049 A | 10/1998 | Ragheb et al. | 623/1 |
| 5,830,178 A | 11/1998 | Jones et al. | 604/49 |
| 5,837,008 A | 11/1998 | Berg et al. | 623/1 |
| 5,837,313 A | 11/1998 | Ding et al. | 427/2.21 |
| 5,849,859 A | 12/1998 | Acemoglu | 528/271 |
| 5,851,508 A | 12/1998 | Greff et al. | 424/9.411 |
| 5,854,376 A | 12/1998 | Higashi | 528/288 |
| 5,858,746 A | 1/1999 | Hubbell et al. | 435/177 |
| 5,865,814 A | 2/1999 | Tuch | 604/265 |
| 5,869,127 A | 2/1999 | Zhong | 427/2.12 |
| 5,873,904 A | 2/1999 | Ragheb et al. | 623/1 |
| 5,876,433 A | 3/1999 | Lunn | 623/1 |
| 5,877,224 A | 3/1999 | Brocchini et al. | 514/772.2 |
| 5,879,713 A | 3/1999 | Roth et al. | 424/489 |
| 5,902,875 A | 5/1999 | Roby et al. | 528/310 |
| 5,905,168 A | 5/1999 | Dos Santos et al. | 562/590 |
| 5,910,564 A | 6/1999 | Gruning et al. | 528/310 |
| 5,914,387 A | 6/1999 | Roby et al. | 528/310 |
| 5,919,893 A | 7/1999 | Roby et al. | 525/411 |
| 5,925,720 A | 7/1999 | Kataoka et al. | 525/523 |
| 5,932,299 A | 8/1999 | Katoot | 427/508 |
| 5,955,509 A | 9/1999 | Webber et al. | 514/772.7 |
| 5,958,385 A | 9/1999 | Tondeur et al. | 424/61 |
| 5,962,138 A | 10/1999 | Kolluri et al. | 428/411.1 |
| 5,971,954 A | 10/1999 | Conway et al. | 604/96 |
| 5,980,928 A | 11/1999 | Terry | 424/427 |
| 5,980,972 A | 11/1999 | Ding | 427/2.24 |
| 5,997,517 A | 12/1999 | Whitbourne | 604/265 |
| 6,010,530 A | 1/2000 | Goicoechea | 623/1 |
| 6,011,125 A | 1/2000 | Lohmeijer et al. | 525/440 |
| 6,015,541 A | 1/2000 | Greff et al. | 424/1.25 |
| 6,033,582 A | 3/2000 | Lee et al. | 216/37 |
| 6,034,204 A | 3/2000 | Mohr et al. | 528/328 |
| 6,042,875 A | 3/2000 | Ding et al. | 427/2.24 |
| 6,051,576 A | 4/2000 | Ashton et al. | 514/255 |
| 6,051,648 A | 4/2000 | Rhee et al. | 525/54.1 |
| 6,054,553 A | 4/2000 | Groth et al. | 528/335 |
| 6,056,993 A | 5/2000 | Leidner et al. | 427/2.25 |
| 6,060,451 A | 5/2000 | DiMaio et al. | 514/13 |
| 6,060,518 A | 5/2000 | Kabanov et al. | 514/781 |
| 6,080,488 A | 6/2000 | Hostettler et al. | 428/423.3 |
| 6,096,070 A | 8/2000 | Ragheb et al. | 623/1 |
| 6,099,562 A | 8/2000 | Ding et al. | 623/1.46 |
| 6,110,188 A | 8/2000 | Narciso, Jr. | 606/153 |
| 6,110,483 A | 8/2000 | Whitbourne et al. | 424/423 |
| 6,113,629 A | 9/2000 | Ken | 623/1.1 |
| 6,120,491 A | 9/2000 | Kohn et al. | 604/502 |
| 6,120,536 A | 9/2000 | Ding et al. | 623/1.43 |
| 6,120,788 A | 9/2000 | Barrows | 424/426 |
| 6,120,904 A | 9/2000 | Hostettler et al. | 428/423.3 |
| 6,121,027 A | 9/2000 | Clapper et al. | 435/180 |
| 6,129,761 A | 10/2000 | Hubbell | 623/11 |
| 6,136,333 A | 10/2000 | Cohn et al. | 424/423 |
| 6,143,354 A | 11/2000 | Koulik et al. | 427/2.24 |
| 6,153,252 A | 11/2000 | Hossainy et al. | 427/2.3 |
| 6,159,978 A | 12/2000 | Myers et al. | 514/252.1 |
| 6,165,212 A | 12/2000 | Dereume et al. | 623/1.13 |
| 6,172,167 B1 | 1/2001 | Stapert et al. | 525/420 |
| 6,177,523 B1 | 1/2001 | Reich et al. | 525/459 |
| 6,180,632 B1 | 1/2001 | Myers et al. | 514/252.1 |
| 6,203,551 B1 | 3/2001 | Wu | 606/108 |
| 6,211,249 B1 | 4/2001 | Cohn et al. | 514/772.1 |
| 6,214,901 B1 | 4/2001 | Chudzik et al. | 523/113 |
| 6,231,600 B1 | 5/2001 | Zhong | 623/1.42 |
| 6,240,616 B1 | 6/2001 | Yan | 29/527.2 |
| 6,245,753 B1 | 6/2001 | Byun et al. | 514/56 |
| 6,245,760 B1 | 6/2001 | He et al. | 514/234.8 |
| 6,248,129 B1 | 6/2001 | Froix | 623/1.42 |
| 6,251,136 B1 | 6/2001 | Guruwaiya et al. | 623/1.46 |
| 6,254,632 B1 | 7/2001 | Wu et al. | 623/1.15 |
| 6,258,121 B1 | 7/2001 | Yang et al. | 623/1.46 |
| 6,258,371 B1 | 7/2001 | Koulik et al. | 424/422 |
| 6,262,034 B1 | 7/2001 | Mathiowitz et al. | 514/44 |
| 6,270,788 B1 | 8/2001 | Koulik et al. | 424/423 |
| 6,277,449 B1 | 8/2001 | Kolluri et al. | 427/289 |
| 6,283,947 B1 | 9/2001 | Mirzaee | 604/264 |
| 6,283,949 B1 | 9/2001 | Roorda | 604/288.02 |
| 6,284,305 B1 | 9/2001 | Ding et al. | 427/2.28 |

| | | | |
|---|---|---|---|
| 6,287,628 B1 | 9/2001 | Hossainy et al. ............. 427/2.3 |
| 6,299,604 B1 | 10/2001 | Ragheb et al. ............. 604/265 |
| 6,306,176 B1 | 10/2001 | Whitbourne ............. 623/23.59 |
| 6,331,313 B1 | 12/2001 | Wong et al. ................. 424/427 |
| 6,335,029 B1 | 1/2002 | Kamath et al. ............. 424/423 |
| 6,344,035 B1 | 2/2002 | Chudzik et al. ............. 604/265 |
| 6,346,110 B2 | 2/2002 | Wu ............................ 606/108 |
| 6,358,556 B1 | 3/2002 | Ding et al. ................ 427/2.24 |
| 6,379,381 B1 | 4/2002 | Hossainy et al. ............ 623/1.42 |
| 6,387,379 B1 | 5/2002 | Goldberg et al. ............ 424/400 |
| 6,395,326 B1 | 5/2002 | Castro et al. ............... 427/2.24 |
| 6,419,692 B1 | 7/2002 | Yang et al. ................. 623/1.15 |
| 6,451,373 B1 | 9/2002 | Hossainy et al. ........... 427/2.25 |
| 6,482,834 B2 | 11/2002 | Spada et al. ............... 514/311 |
| 6,494,862 B1 | 12/2002 | Ray et al. ................. 604/96.01 |
| 6,503,538 B1 | 1/2003 | Chu et al. .................. 424/497 |
| 6,503,556 B2 | 1/2003 | Harish et al. ............. 427/2.24 |
| 6,503,954 B1 | 1/2003 | Bhat et al. ............... 514/772.2 |
| 6,506,437 B1 | 1/2003 | Harish et al. ............. 427/2.25 |
| 6,524,347 B1 | 2/2003 | Myers et al. |
| 6,527,801 B1 | 3/2003 | Dutta ........................ 623/1.46 |
| 6,527,863 B1 | 3/2003 | Pacetti et al. ................ 118/500 |
| 6,528,526 B1 | 3/2003 | Myers et al. ................. 214/311 |
| 6,530,950 B1 | 3/2003 | Alvarado et al. ............ 623/1.13 |
| 6,530,951 B1 | 3/2003 | Bates et al. ................ 623/1.45 |
| 6,540,776 B2 | 4/2003 | Sanders Millare et al. . 623/1.15 |
| 6,544,223 B1 | 4/2003 | Kokish ................... 604/103.01 |
| 6,544,543 B1 | 4/2003 | Mandrusov et al. ......... 424/422 |
| 6,544,582 B1 | 4/2003 | Yoe ............................. 27/2.24 |
| 6,555,157 B1 | 4/2003 | Hossainy ................... 427/2.24 |
| 6,558,733 B1 | 5/2003 | Hossainy et al. ........... 427/2.24 |
| 6,565,659 B1 | 5/2003 | Pacetti et al. ................ 118/500 |
| 6,572,644 B1 | 6/2003 | Moein ...................... 623/1.11 |
| 6,585,755 B2 | 7/2003 | Jackson et al. ............. 623/1.15 |
| 6,585,765 B1 | 7/2003 | Hossainy et al. ........... 623/1.45 |
| 6,585,926 B1 | 7/2003 | Mirzaee ..................... 264/400 |
| 6,605,154 B1 | 8/2003 | Villareal ..................... 118/500 |
| 6,616,765 B1 | 9/2003 | Wu et al. ................... 623/1.45 |
| 6,623,448 B2 | 9/2003 | Slater .................... 604/95.01 |
| 6,625,486 B2 | 9/2003 | Lundkvist et al. ............. 604/21 |
| 6,645,135 B1 | 11/2003 | Bhat ............................. 600/3 |
| 6,645,195 B1 | 11/2003 | Bhat et al. .................. 604/528 |
| 6,656,216 B1 | 12/2003 | Hossainy et al. ........... 623/1.13 |
| 6,656,506 B1 | 12/2003 | Wu et al. ................... 424/489 |
| 6,660,034 B1 | 12/2003 | Mandrusov et al. ........ 623/1.42 |
| 6,663,662 B2 | 12/2003 | Pacetti et al. ............... 623/1.13 |
| 6,663,880 B1 | 12/2003 | Roorda et al. ............. 424/423 |
| 6,666,880 B1 | 12/2003 | Chiu et al. ................. 623/1.11 |
| 6,673,154 B1 | 1/2004 | Pacetti et al. ................ 118/500 |
| 6,673,385 B1 | 1/2004 | Ding et al. ................ 427/2.28 |
| 6,689,099 B2 | 2/2004 | Mirzaee ..................... 604/107 |
| 6,695,920 B1 | 2/2004 | Pacetti et al. ................ 118/500 |
| 6,706,013 B1 | 3/2004 | Bhat et al. ................ 604/96.01 |
| 6,709,514 B1 | 3/2004 | Hossainy ................... 118/52 |
| 6,712,845 B2 | 3/2004 | Hossainy ................... 623/1.42 |
| 6,713,119 B2 | 3/2004 | Hossainy et al. ........... 427/2.25 |
| 6,716,444 B1 | 4/2004 | Castro et al. ............... 424/422 |
| 6,723,120 B2 | 4/2004 | Yan ........................... 623/1.15 |
| 6,733,768 B2 | 5/2004 | Hossainy et al. ........... 424/426 |
| 6,740,040 B1 | 5/2004 | Mandrusov et al. ........ 600/439 |
| 6,743,462 B1 | 6/2004 | Pacetti ...................... 427/2.24 |
| 6,749,626 B1 | 6/2004 | Bhat et al. ................. 623/1.1 |
| 6,753,071 B1 | 6/2004 | Pacetti et al. ................ 428/212 |
| 6,758,859 B1 | 7/2004 | Dang et al. ................. 623/1.15 |
| 6,759,054 B2 | 7/2004 | Chen et al. ................. 424/423 |
| 6,764,505 B1 | 7/2004 | Hossainy et al. ........... 623/1.15 |
| 7,491,233 B1 | 2/2009 | Ding et al. |
| 2001/0000230 A1 | 4/2001 | Bernstein et al. |
| 2001/0007083 A1 | 7/2001 | Roorda ..................... 623/1.15 |
| 2001/0009656 A1 | 7/2001 | Greff et al. |
| 2001/0014717 A1 | 8/2001 | Hossainy et al. ............. 525/60 |
| 2001/0018469 A1 | 8/2001 | Chen et al. .................. 523/121 |
| 2001/0020011 A1 | 9/2001 | Mathiowitz et al. ........... 514/44 |
| 2001/0029351 A1 | 10/2001 | Falotico et al. .......... 604/103.02 |
| 2001/0037145 A1 | 11/2001 | Guruwaiya et al. ......... 623/1.15 |
| 2001/0051608 A1 | 12/2001 | Mathiowitz et al. ........... 514/44 |
| 2002/0005206 A1 | 1/2002 | Falotico et al. ............... 128/898 |
| 2002/0007213 A1 | 1/2002 | Falotico et al. ............. 623/1.21 |
| 2002/0007214 A1 | 1/2002 | Falotico ................... 623/1.21 |
| 2002/0007215 A1 | 1/2002 | Falotico et al. ............. 623/1.21 |
| 2002/0009604 A1 | 1/2002 | Zamora et al. .............. 428/450 |
| 2002/0016625 A1 | 2/2002 | Falotico et al. ............. 623/1.13 |
| 2002/0031616 A1 | 3/2002 | Neoh et al. |
| 2002/0032414 A1 | 3/2002 | Ragheb et al. ............. 604/265 |
| 2002/0032434 A1 | 3/2002 | Chudzik et al. ........... 604/890.1 |
| 2002/0051730 A1 | 5/2002 | Bodnar et al. ................. 422/33 |
| 2002/0071822 A1 | 6/2002 | Uhrich ..................... 424/78.37 |
| 2002/0077693 A1 | 6/2002 | Barclay et al. ............. 623/1.13 |
| 2002/0082679 A1 | 6/2002 | Sirhan et al. ............... 623/1.15 |
| 2002/0087123 A1 | 7/2002 | Hossainy et al. ........... 604/198 |
| 2002/0091230 A1 | 7/2002 | Mao et al. |
| 2002/0091433 A1 | 7/2002 | Ding et al. ................. 623/1.2 |
| 2002/0094440 A1 | 7/2002 | Llanos et al. ............... 428/421 |
| 2002/0111590 A1 | 8/2002 | Davila et al. ................ 604/265 |
| 2002/0120326 A1 | 8/2002 | Michal ..................... 623/1.15 |
| 2002/0123801 A1 | 9/2002 | Pacetti et al. ............... 623/1.46 |
| 2002/0142039 A1 | 10/2002 | Claude ...................... 424/486 |
| 2002/0155212 A1 | 10/2002 | Hossainy ................... 427/2.25 |
| 2002/0165608 A1 | 11/2002 | Llanos et al. ............... 623/1.45 |
| 2002/0176849 A1 | 11/2002 | Slepian ...................... 424/93.7 |
| 2002/0183581 A1 | 12/2002 | Yoe et al. ....................... 600/3 |
| 2002/0188037 A1 | 12/2002 | Chudzik et al. ............. 523/112 |
| 2002/0188277 A1 | 12/2002 | Roorda et al. ............... 604/523 |
| 2003/0004141 A1 | 1/2003 | Brown ....................... 514/152 |
| 2003/0028243 A1 | 2/2003 | Bates et al. ................. 623/1.15 |
| 2003/0028244 A1 | 2/2003 | Bates et al. ................. 623/1.15 |
| 2003/0031780 A1 | 2/2003 | Chudzik et al. .............. 427/2.1 |
| 2003/0032767 A1 | 2/2003 | Tada et al. .................. 528/310 |
| 2003/0036794 A1 | 2/2003 | Ragheb et al. ............. 623/1.15 |
| 2003/0039689 A1 | 2/2003 | Chen et al. .................. 424/468 |
| 2003/0040712 A1 | 2/2003 | Ray et al. ................... 604/173 |
| 2003/0040790 A1 | 2/2003 | Furst ....................... 623/1.11 |
| 2003/0059520 A1 | 3/2003 | Chen et al. ................... 427/2.1 |
| 2003/0060877 A1 | 3/2003 | Falotico et al. ............. 623/1.42 |
| 2003/0065377 A1 | 4/2003 | Davila et al. ............... 623/1.13 |
| 2003/0072868 A1 | 4/2003 | Harish et al. ............. 427/2.24 |
| 2003/0073961 A1 | 4/2003 | Happ ....................... 604/274 |
| 2003/0083646 A1 | 5/2003 | Sirhan et al. ............... 604/891.1 |
| 2003/0083739 A1 | 5/2003 | Cafferata ................... 623/1.42 |
| 2003/0097088 A1 | 5/2003 | Pacetti ....................... 604/19 |
| 2003/0097173 A1 | 5/2003 | Dutta ........................ 623/1.38 |
| 2003/0099712 A1 | 5/2003 | Jayaraman ................ 424/486 |
| 2003/0105518 A1 | 6/2003 | Dutta ........................ 623/1.38 |
| 2003/0113439 A1 | 6/2003 | Pacetti et al. ............... 427/2.24 |
| 2003/0150380 A1 | 8/2003 | Yoe .......................... 118/423 |
| 2003/0157241 A1 | 8/2003 | Hossainy et al. ........... 427/2.24 |
| 2003/0158517 A1 | 8/2003 | Kokish .................... 604/103.01 |
| 2003/0190406 A1 | 10/2003 | Hossainy et al. ........... 427/2.25 |
| 2003/0207020 A1 | 11/2003 | Villareal .................... 427/2.24 |
| 2003/0211230 A1 | 11/2003 | Pacetti et al. ............... 427/2.24 |
| 2004/0018296 A1 | 1/2004 | Castro et al. ............... 427/2.25 |
| 2004/0029952 A1 | 2/2004 | Chen et al. ................. 514/449 |
| 2004/0034409 A1 | 2/2004 | Heublein et al. |
| 2004/0047978 A1 | 3/2004 | Hossainy et al. ............. 427/2.1 |
| 2004/0047980 A1 | 3/2004 | Pacetti et al. ............... 427/2.25 |
| 2004/0052858 A1 | 3/2004 | Wu et al. ................... 424/490 |
| 2004/0052859 A1 | 3/2004 | Wu et al. ................... 424/490 |
| 2004/0054104 A1 | 3/2004 | Pacetti ...................... 526/242 |
| 2004/0060508 A1 | 4/2004 | Pacetti et al. ................ 118/264 |
| 2004/0062853 A1 | 4/2004 | Pacetti et al. ............... 427/2.1 |
| 2004/0063663 A1 | 4/2004 | Buchanan et al. |
| 2004/0063805 A1 | 4/2004 | Pacetti et al. ............... 523/113 |
| 2004/0071861 A1 | 4/2004 | Mandrusov et al. ........ 427/2.24 |
| 2004/0072922 A1 | 4/2004 | Hossainy et al. ........... 523/113 |
| 2004/0073298 A1 | 4/2004 | Hossainy ................... 623/1.46 |
| 2004/0086542 A1 | 5/2004 | Hossainy et al. ........... 424/423 |

| | | | | | | |
|---|---|---|---|---|---|---|
| 2004/0086550 | A1 | 5/2004 | Roorda et al. ............... 424/448 | WO | WO 03/037223 | 5/2003 |
| 2004/0096504 | A1 | 5/2004 | Michal ....................... 424/471 | WO | WO 03/039612 | 5/2003 |
| 2004/0098117 | A1 | 5/2004 | Hossainy et al. ........... 623/1.42 | WO | WO 03/080147 | 10/2003 |
| 2005/0106203 | A1 | 5/2005 | Roorda et al. | WO | WO 03/082368 | 10/2003 |
| | | | | WO | WO 04/000383 | 12/2003 |

FOREIGN PATENT DOCUMENTS

| | | |
|---|---|---|
| EP | 0 301 856 | 2/1989 |
| EP | 0 396 429 | 11/1990 |
| EP | 0 514 406 | 11/1992 |
| EP | 0 604 022 | 6/1994 |
| EP | 0 623 354 | 11/1994 |
| EP | 0 665 023 | 8/1995 |
| EP | 0 701 802 | 3/1996 |
| EP | 0 716 836 | 6/1996 |
| EP | 0 809 999 | 12/1997 |
| EP | 0 832 655 | 4/1998 |
| EP | 0 850 651 | 7/1998 |
| EP | 0 879 595 | 11/1998 |
| EP | 0 910 584 | 4/1999 |
| EP | 0 923 953 | 6/1999 |
| EP | 0 953 320 | 11/1999 |
| EP | 0 970 711 | 1/2000 |
| EP | 0 982 041 | 3/2000 |
| EP | 1 023 879 | 8/2000 |
| EP | 1 192 957 | 4/2002 |
| EP | 1 273 314 | 1/2003 |
| JP | 2001-190687 | 7/2001 |
| SU | 872531 | 10/1981 |
| SU | 876663 | 10/1981 |
| SU | 905228 | 2/1982 |
| SU | 790725 | 2/1983 |
| SU | 1016314 | 5/1983 |
| SU | 811750 | 9/1983 |
| SU | 1293518 | 2/1987 |
| WO | WO 91/12846 | 9/1991 |
| WO | WO 94/09760 | 5/1994 |
| WO | WO 95/10989 | 4/1995 |
| WO | WO 95/24929 | 9/1995 |
| WO | WO 96/40174 | 12/1996 |
| WO | WO 97/10011 | 3/1997 |
| WO | WO 97/45105 | 12/1997 |
| WO | WO 97/46590 | 12/1997 |
| WO | WO 98/08463 | 3/1998 |
| WO | WO 98/17331 | 4/1998 |
| WO | WO 98/32398 | 7/1998 |
| WO | WO 98/32777 | 7/1998 |
| WO | WO 98/36784 | 8/1998 |
| WO | WO 99/01118 | 1/1999 |
| WO | WO 99/38546 | 8/1999 |
| WO | WO 99/63981 | 12/1999 |
| WO | WO 00/02599 | 1/2000 |
| WO | WO 00/12147 | 3/2000 |
| WO | WO 00/18446 | 4/2000 |
| WO | WO 00/56376 | 9/2000 |
| WO | WO 00/64506 | 11/2000 |
| WO | WO 01/01890 | 1/2001 |
| WO | WO 01/15751 | 3/2001 |
| WO | WO 01/17577 | 3/2001 |
| WO | WO 01/45763 | 6/2001 |
| WO | WO 01/49338 | 7/2001 |
| WO | WO 01/51027 | 7/2001 |
| WO | WO 01/74414 | 10/2001 |
| WO | WO 02/03890 | 1/2002 |
| WO | WO 02/18477 | 3/2002 |
| WO | WO 02/26162 | 4/2002 |
| WO | WO 02/34311 | 5/2002 |
| WO | WO 02/056790 | 7/2002 |
| WO | WO 02/058753 | 8/2002 |
| WO | WO 02/102283 | 12/2002 |
| WO | WO 03/000308 | 1/2003 |
| WO | WO 03/022323 | 3/2003 |
| WO | WO 03/028780 | 4/2003 |
| WO | WO 2004/009145 | 1/2004 |
| WO | WO 2004/014449 | 2/2004 |
| WO | WO 2004/022119 | 3/2004 |
| WO | WO 2005/011770 | 2/2005 |
| WO | WO 2005/039489 | 5/2005 |
| WO | WO 2005/042600 | 5/2005 |
| WO | WO 2005/051445 | 6/2005 |
| WO | WO 2005/066241 | 7/2005 |
| WO | WO 2005/089824 | 9/2005 |

OTHER PUBLICATIONS

Anonymous, *Heparin-coated stents cut complications by 30%*, Clinica 732:17 (Nov. 18, 1996), http://www.dialogweb.com/cqi/document?req=1061847871753, printed Aug. 25, 2003 (2 pages).

Anonymous, *Rolling Therapeutic Agent Loading Device for Therapeutic Agent Delivery or Coated Stent* (Abstract 434009), Res. Disclos. pp. 974-975 (Jun. 2000).

Anonymous, *Stenting continues to dominate cardiology*, Clinica 720:22 (Sep. 2, 1996), http://www.dialogweb.com/cgi/document?req=1061848017752, printed Aug. 25, 2003 (2 pages).

Aoyagi et al., *Preparation of cross-linked aliphatic polyester and application to thermo-responsive material*, Journal of Controlled Release 32:87-96 (1994).

Barath et al., *Low Dose of Antitumor Agents Prevents Smooth Muscle Cell Proliferation After Endothelial Injury*, JACC 13(2): 252A (Abstract) (Feb. 1989).

Barbucci et al., *Coating of commercially available materials with a new heparinizable material*, J. Biomed. Mater. Res. 25:1259-1274 (Oct. 1991).

Chung et al., *Inner core segment design for drug delivery control of thermo-responsive polymeric micelles*, Journal of Controlled Release 65:93-103 (2000).

Dev et al., *Kinetics of Drug Delivery to the Arterial Wall Via Polyurethane-Coated Removable Nitinol Stent: Comparative Study of Two Drugs*, Catheterization and Cardiovascular Diagnosis 34:272-278 (1995).

Dichek et al., *Seeding of Intravascular Stents with Genetically Engineered Endothelial Cells*, Circ. 80(5):1347-1353 (Nov. 1989).

Eigler et al., *Local Arterial Wall Drug Delivery from a Polymer Coated Removable Metallic Stent: Kinetics, Distribution, and Bioactivity of Forskolin*, JACC, 4A (701-1), Abstract (Feb. 1994).

Helmus, *Overview of Biomedical Materials*, MRS Bulletin, pp. 33-38 (Sep. 1991).

Herdeg et al., *Antiproliferative Stent Coatings: Taxol and Related Compounds*, Semin. Intervent. Cardiol. 3:197-199 (1998).

Huang et al., *Biodegradable Polymers Derived from Aminoacids*, Macromol. Symp. 144, 7-32 (1999).

Inoue et al., *An AB block copolymer of oligo(methyl methacrylate) and poly(acrylic acid) for micellar delivery of hydrophobic drugs*, Journal of Controlled Release 51:221-229 (1998).

Kataoka et al., *Block copolymer micelles as vehicles for drug delivery*, Journal of Controlled Release 24:119-132 (1993).

Katsarava et al., *Amino Acid-Based Bioanalogous Polymers. Synthesis and Study of Regular Poly(ester amide)s Based on Bis(α-amino acid)α,ω-Alkylene Diesters, and Aliphatic Dicarboxylic Acids*, Journal of Polymer Science, Part A: Polymer Chemistry, 37(4), 391-407 (1999).

Levy et al., *Strategies for Treating Arterial Restenosis Using Polymeric Controlled Release Implants*, Biotechnol. Bioact. Polym. [Proc. Am. Chem. Soc. Symp.], pp. 259-268 (1994).

Liu et al., *Drug release characteristics of unimolecular polymeric micelles*, Journal of Controlled Release 68:167-174 (2000).

Marconi et al., *Covalent bonding of heparin to a vinyl copolymer for biomedical applications*, Biomaterials 18(12):885-890 (1997).

Matsumaru et al., *Embolic Materials for Endovascular Treatment of Cerebral Lesions*, J. Biomater. Sci. Polymer Edn 8(7):555-569 (1997).

Miyazaki et al., *Antitumor Effect of Implanted Ethylene-Vinyl Alcohol Copolymer Matrices Containing Anticancer Agents on Ehrlich Ascites Carcinoma and P388 Leukemia in Mice*, Chem. Pharm. Bull. 33(6) 2490-2498 (1985).

Miyazawa et al., *Effects of Pemirolast and Tranilast on Intimal Thickening After Arterial Injury in the Rat*, J. Cardiovasc. Pharmacol., pp. 157-162 (1997).

Nordrehaug et al., *A novel biocompatible coating applied to coronary stents*, European Heart Journal 14, p. 321 (P1694), Abstr. Suppl. (1993).

Ohsawa et al., *Preventive Effects of an Antiallergic Drug, Pemirolast Potassium, on Restenosis After Percutaneous Transluminal Coronary Angioplasty*, American Heart Journal 136(6):1081-1087 (Dec. 1998).

Ozaki et al., *New Stent Technologies*, Progress in Cardiovascular Diseases, Vol. XXXIX(2):129-140 (Sep./Oct. 1996).

Pechar et al., *Poly(ethylene glycol) Multiblock Copolymer as a Carrier of Anti-Cancer Drug Doxorubicin*, Bioconjucate Chemistry 11(2):131-139 (Mar./Apr. 2000).

Peng et al., *Role of polymers in improving the results of stenting in coronary arteries*, Biomaterials 17:685-694 (1996).

Saotome, et al., *Novel Enzymatically Degradable Polymers Comprising α-Amino Acid, 1,2-Ethanediol, and Adipic Acid*, Chemistry Letters, pp. 21-24, (1991).

Shigeno, *Prevention of Cerebrovascular Spasm by Bosentan, Novel Endothelin Receptor*, Chemical Abstract 125:212307 (1996).

van Beusekom et al., *Coronary stent coatings*, Coronary Artery Disease 5(7):590-596 (Jul. 1994).

Wilensky et al., *Methods and Devices for Local Drug Delivery in Coronary and Peripheral Arteries*, Trends Cardiovasc. Med. 3(5):163-170 (1993).

Yokoyama et al. *Characterization of physical entrapment and chemical conjugation of adriamycin in polymeric micelles and their design for in vivo delivery to a solid tumor*, Journal of Controlled Release 50:79-92 (1998).

European Search Report for 05741085.4, mailed Jul. 16, 2007, 13 pgs.

\* cited by examiner

METHOD AND SYSTEM OF CONTROLLED TEMPERATURE MIXING AND MOLDING OF POLYMERS WITH ACTIVE AGENTS FOR IMPLANTABLE MEDICAL DEVICES

CROSS-REFERENCE

This is a continuation-in-part of application Ser. No. 10/631,228 filed on Jul. 31, 2003, now U.S. Pat. No. 7,645,474.

BACKGROUND OF THE INVENTION

1. Field of the Invention

This invention is directed to methods and systems for purifying polymers and mixing polymers with active agents used for medical devices, such as drug eluting and/or delivery stents.

2. Description of the State of the Art

Polymeric materials have a variety of applications in the medical field, including with stents. Metallic stents are being coated with a polymeric material for local delivery of a drug or therapeutic substance. Stents are also being made from polymeric materials that are bioabsorbable or bioerodable so as to maintain vascular patency for a desired duration of time until they are absorbed or degraded and eliminated by the body. Biodegradable stents can also contain or carry therapeutic substances. Polymers can contain impurities that trigger adverse biological responses when implanted into the body. Polymers can contain impurities such as catalysts, initiators, processing aids, suspension aids, unreacted monomers and oligomers or other low molecular weight species, even though the polymer may be classified as a "food packaging grade" polymer by the manufacturer. Accordingly, there is a need for purifying polymers for medical applications.

In addition to containing impurities, another impediment faced with drug eluting and/or delivery stents is the inconsistency of replicating stents having the same drug profile or producing a stent having a homogeneous or substantially homogenous drug concentration throughout the stent body or a segment of the body of the stent. "Homogeneous" may be defined as uniform in chemical composition, appearance and properties. Current processes can lead to non-homogeneous polymer-drug compositions that form higher concentration of drugs on certain parts of a stent than other areas of the stent. For example, a coating for a drug-eluting and/or delivery stent is typically prepared by dissolving a polymer and a drug in a suitable solvent or combination of solvents. The polymer and active agent may be dissolved together or separately in their respective solvents then added together. The latter is a more effective technique if the polymer and the drug cannot be easily blended. Operations such as stirring, heating and/or agitation are employed to combine the polymer with the active agent. The foregoing method of blending the polymer and the active agent does not produce a desired degree of homogeneity. The difference in density between the active agent and the polymer may make adequate mixing of the ingredients difficult to achieve. Inadequate mixing may result in a coating with different active agent concentration in various portions of the body of the device. Consistency is replication is also compromised.

Furthermore, heating of the composition may be needed to effect dissolution. Some drugs degrade or diminish in property when exposed to elevated temperatures. The degradation of drugs also depends on the time of exposure. Therefore, it is important that an agitation method limit exposure of a polymer and the active agent solution to high temperatures and the time the solution is exposed to such temperatures. The embodiments of the present invention address these as well as other needs.

SUMMARY

In accordance with one aspect of the invention, a method of making a composition for use in manufacturing a drug-eluting and/or delivery implantable medical device is disclosed. The method includes introducing a polymer into a mixing apparatus such as an extruder. The method further includes introducing an active agent into the mixing apparatus, introducing a solvent into the mixing apparatus, mixing the active agent with the polymer in the apparatus to form a polymer mixture, mixing the solvent with the polymer in the apparatus, controlling a temperature of the polymer mixture in at least a portion of the apparatus, and removing the polymer mixture from the apparatus. In an embodiment, the polymer mixture is for use as a coating for an implantable medical device, or fabricating an implantable medical device. The invention also includes a composition formed by the method described above.

A further aspect of the invention is disclosed which includes a system for use in manufacturing an implantable medical device. The system includes an extruder. The extruder includes a first port configured to receive a polymer; a second port configured to receive an active agent; an element configured to convey the polymer through the extruder and configured to form a polymer mixture including the polymer and an active agent; and a third port configured to eject the polymer mixture comprising the active agent.

DETAILED DESCRIPTION

Methods of Purification

Figure 1:
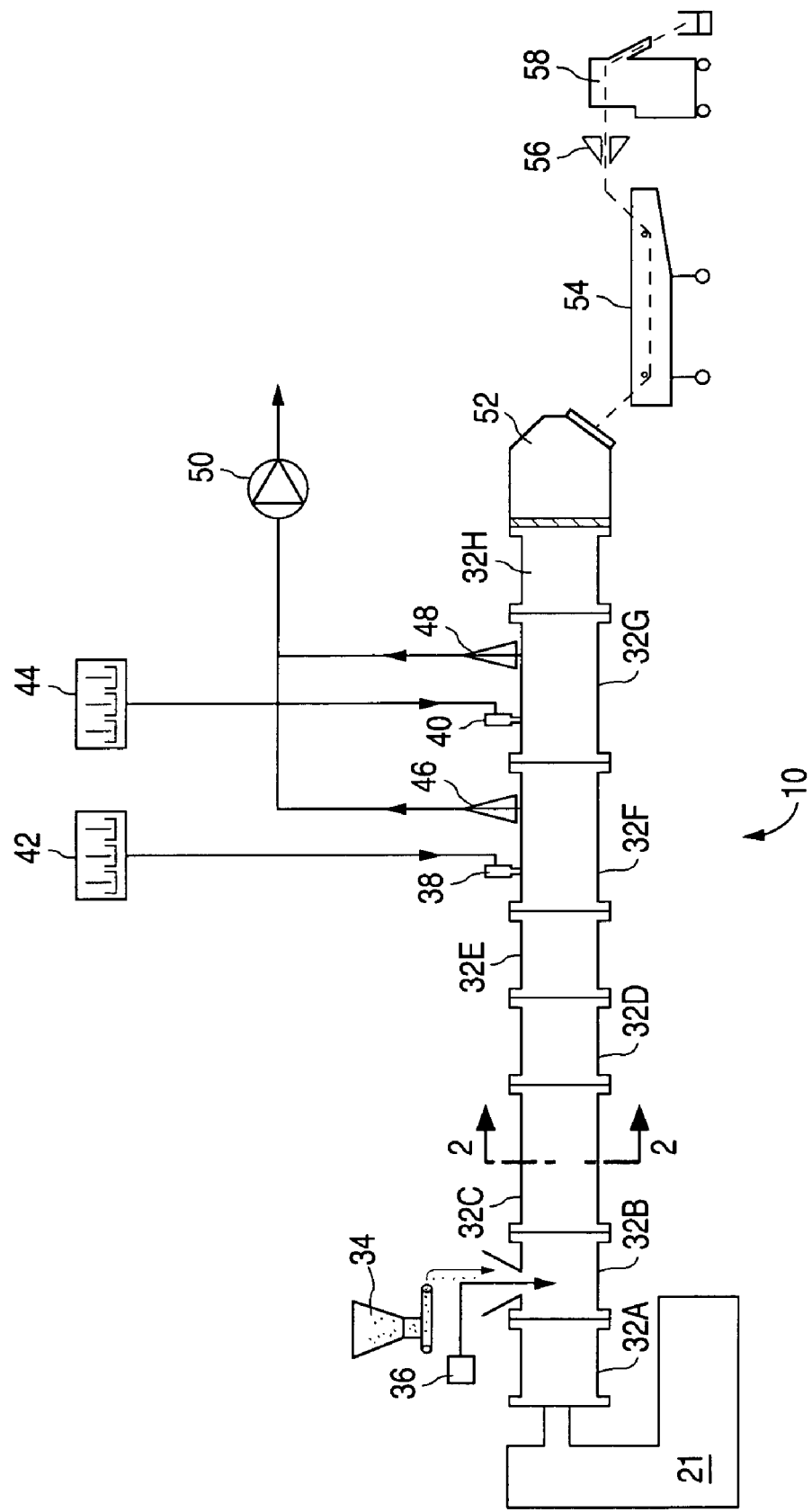
FIG. 1 is an illustration of a system including a twin screw extruder for purifying a polymer in accordance with an embodiment of the present invention.

Before a polymer is used to make or coat an implantable medical device, the polymer should be purified. The present invention provides a method of purifying a polymer (e.g., thermoplastic polymer) for use with an implantable medical device. The method includes introducing a polymer having an impurity into a mixing apparatus. The method can include reducing the viscosity of the polymer to produce a workable range of viscosity, for example, so that the polymer is in a liquid form or state. Next, a fluid is introduced into the mixing apparatus and mixed with the liquid form of the polymer. As the fluid is mixed with the polymer, the fluid acts to strip or, remove impurities from the polymer. After the impurities have been removed from the polymer by the fluid, the fluid containing the impurity is removed from the mixing apparatus and the purified polymer is collected. By using the methods of the present invention, polymers can be purified to remove a significant amount of low molecular weight species such as residual catalysts, initiators, processing aids, suspension aids, unreacted monomers and oligomers.

Polymers can be biostable, bioabsorbable, biodegradable or bioerodable. The terms biodegradable, bioabsorbable, and bioerodable are used interchangeably and refer to polymers that are capable of being completely degraded and/or eroded when exposed to bodily fluids such as blood and can be gradually resorbed, absorbed and/or eliminated by the body. The processes of breaking down and eventual absorption and elimination of the polymer can be caused by, for example, hydrolysis, metabolic processes, bulk or surface erosion, and the like. For coating applications, it is understood that after the process of degradation, erosion, absorption, and/or resorption has been completed, no polymer will remain on the device. In some embodiments, very negligible traces or residue may be left behind. For stents made from a biodegradable polymer, the stent is intended to remain in the body for a duration of time until its intended function of, for example, maintaining vascular patency and/or drug eluting and/or delivery is accomplished.

Representative examples of polymers that can be purified by using the methods of the present invention include poly (N-acetylglucosamine) (Chitin), Chitoson, poly(hydroxyvalerate), poly(lactide-co-glycolide), poly(hydroxybutyrate), poly(hydroxybutyrate-co-valerate), polyorthoester, polyanhydride, poly(glycolic acid), poly(D,L-lactic acid), poly(glycolic acid-co-trimethylene carbonate), poly(trimethylene carbonate), co-poly(ether-esters) (e.g. PEO/PLA), polyphosphazenes, biomolecules (such as fibrin, fibrinogen, cellulose, starch, collagen and hyaluronic acid), polyurethanes, silicones, polyesters, polyolefins, polyisobutylene and ethylene-alphaolefin copolymers, acrylic polymers and copolymers other than polyacrylates, vinyl halide polymers and copolymers (such as polyvinyl chloride), polyvinyl ethers (such as polyvinyl methyl ether), polyvinylidene halides (such as polyvinylidene chloride), polyacrylonitrile, polyvinyl ketones, polyvinyl aromatics (such as polystyrene), polyvinyl esters (such as polyvinyl acetate), acrylonitrile-styrene copolymers, ABS resins, polyamides (such as Nylon 66 and polycaprolactam), polycarbonates, polyoxymethylenes, polyimides, polyethers, polyurethanes, rayon, rayon-triacetate, cellulose, cellulose acetate, cellulose butyrate, cellulose acetate butyrate, cellophane, cellulose nitrate, cellulose propionate, cellulose ethers, and carboxymethyl cellulose.

Representative examples of polymers that can be especially well suited for purification by using a method of the present invention include ethylene vinyl alcohol copolymer (commonly known by the generic name EVOH or by the trade name EVAL), poly(butyl methacrylate), poly(vinylidene fluoride-co-hexafluororpropene) (e.g., SOLEF 21508, available from Solvay Solexis PVDF, Thorofare, N.J.), polyvinylidene fluoride (otherwise known as KYNAR, available from ATOFINA Chemicals, Philadelphia, Pa.), poly(L-lactic acid), poly(caprolactone), ethylene-vinyl acetate copolymers, polyethylene glycol.

A polymer having an impurity can be introduced into a mixing apparatus in a solid form (e.g., such as pellets or a fine powder) or a melted form (e.g., as a polymer pre-heated to a temperature at or above the melting temperature of the polymer). As the polymer is introduced into the mixing device, or any time during the purification process, a gas can be delivered to the mixing device to reduce the amount of degradation or discoloration experienced by the polymer. The gas can reduce the amount of degradation or discoloration by removing degradation agents. For example, the gas can remove atmospheric oxygen from the mixing apparatus. Atmospheric oxygen, if not removed from the mixing apparatus, can cause discoloration during the purification process. Representative examples of gases that can be delivered include inert gases such as nitrogen, argon, etc.

As the polymer is mixed in the mixing apparatus, the polymer should be in a substantially liquid form. The viscosity of the polymer in the mixing apparatus can be at the maximum, about 10,000 poises at 1 atm to about 20,000 poises at 1 atm. If the polymer is too viscous (e.g., has been introduced into the mixing apparatus as a solid form), the polymer should be exposed to mixing conditions that decrease the viscosity. For example, the mixing parameters (e.g., shear rate) can be selected so that the polymer's viscosity is decreased. Also, the polymer can be exposed to a sufficient temperature that decreases the viscosity of the polymer. For instance, the polymer can be heated by elements integrated with the mixing apparatus to a temperature equal to or greater than the temperature at which the polymer exhibits characteristics of a liquid such as the ability to flow. In one embodiment, the polymer is exposed to a temperature equal to or greater than the melting temperature of the polymer. The melting temperature of a crystalline or semi-crystalline polymer is the temperature at which the last trace of crystallinity in the polymer disappears as a sample is exposed to increasing heat. The melting temperature of a polymer is also known as the fusion temperature. Methods of measuring melting temperatures are understood by one of ordinary skill in the art and are discussed by, for example, L. H. Sperling, Introduction to Physical Polymer Science, Wiley-Interscience, New York (3rd ed. 2001), and R. F. Boyer, in Encyclopedia of Polymer Science and Technology, Suppl. Vol. 2, N. M. Bikales, ed., Interscience, New York (1977).

In the next step of the process, a fluid is introduced into the mixing apparatus. The fluid acts to strip or remove the impurity from the polymer. The fluid can be introduced into the mixing apparatus in either a liquid or gas/vapor form. Additionally, more than one fluid can be introduced into the mixing apparatus. Representative injection rates of the fluid can be from about 100 ml/hr to about 1200 ml/hr, and more narrowly 490 ml/hr to 1000 ml/hr.

The fluid can be selected in order to remove the known or suspected impurity in the polymer. For example, impurities such as sodium acetate, and lower molecular weight monomers and oligomers can be removed from an ethylene vinyl alcohol copolymer. Without being bound by any particular theory, it is believed that the fluid can remove an impurity because the fluid can dissolve the impurity and thus remove the impurity from the polymer mass. On the other hand, it is also believed that some fluids are capable of removing an impurity by physically entrapping the impurity without dissolving the impurity or only partially dissolving the impurity. In other words, it is believed that the fluid can physically force the impurity out of the polymer and to the surface of the polymer mass, where the impurity can be extracted from the mixing apparatus.

In one embodiment of the present invention, two different fluids are used to extract an impurity. A first fluid is capable of acting as a solvent for the impurity. For example, inorganic salts such as state salt and sodium acetate can be removed from poly(butyl methacrylate) by being dissolved in water. "Solvent" is defined as a substance capable of dissolving or dispersing one or more other substances or capable of at least partially dissolving or dispersing the substance(s) to form a uniformly dispersed mixture at the molecular- or ionic-size level. The solvent should be capable of dissolving at least 0.1 mg of the impurity in 1 ml of the solvent, and more narrowly 0.5 mg in 1 ml at ambient temperature and ambient pressure.

A second fluid can act as a non-solvent for the impurity. For example, low molecular weight components (i.e., molecules having less than 1000 daltons) can be removed by being suspended by water. "Non-solvent" is defined as a substance incapable of dissolving the other substance. The non-solvent should be capable of dissolving only less than 0.1 mg of the impurity in 1 ml of the non-solvent at ambient temperature and ambient pressure, and more narrowly only less than 0.05 mg in 1 ml at ambient temperature and ambient pressure.

Representative examples of fluids that can remove an impurity include nitrogen, argon, air, water, isopropyl alcohol, methanol, FLUX REMOVER AMS, acetone, ethanol, dimethyl acetamide (DMAC), acetonitrile, dimethyl formamide (DMF), cyclohexane, dimethyl sulfoxide (DMSO), and mixtures thereof. FLUX REMOVER AMS is a trade name of a solvent manufactured by Tech Spray, Inc. of Amarillo, Tex. comprising about 93.7% of a mixture of 3,3-dichloro-1,1,1, 2,2-pentafluoropropane and 1,3-dichloro-1,1,2,2,3-pentafluoropropane, and the balance methanol, with trace amounts of nitromethane.

After the fluid has removed the impurity from the polymer mass, if the fluid is in a liquid form, then the fluid is heated to a temperature equal to or greater than the boiling point of the fluid at ambient pressure. The fluid in the vapor form containing the impurity is removed from the mixing apparatus. The fluid containing the impurity can be allowed to evaporate from the mixing apparatus under 1 atm, or the fluid can be extracted under a vacuum or reduced pressure, for example a pressure less than less than about 300 mm Hg, or more narrowly, less than about 10 mm Hg.

The following Table 1 provides selected properties for representative examples of fluids:

TABLE 1

| FLUID | VAPOR PRESSURE (mm Hg) @ 20° C. | BOILING POINT (° C.) @ 1 atm |
|---|---|---|
| Water | 17.5 | 100 |
| Isopropyl alcohol | 32.4 | 82 |
| Methanol | 97 | 65 |
| DMAC | 1.3 | 166 |
| Acetone | 185 | 56 |
| Ethanol | 40 | 78 |
| DMSO | 0.6 | 189 |
| DMF | 2.7 | 153 |
| Cyclohexane | 77.5 | 49 |

After the impurity has been removed from the polymer, the purified polymer can be collected from the mixing apparatus. For example, the purified polymer can be pressurized and discharged from the mixing apparatus through a die. Additionally, the purified polymer can be extracted into a cooling bath or a stainless steel conveyer belt in preparation for post-processing.

System for Polymer Purification

Representative examples of mixing apparatuses for the present invention include single screw extruders, intermeshing co-rotating and counter-rotating twin-screw extruders and other multiple screw masticating extruders. FIG. 1 illustrates an example of a twin screw extruder 10. The configuration illustrated in FIG. 1 is an intermeshing co-rotating twin screw extruder. However, other configurations for a twin screw extruder are contemplated as useful with the process of the present invention, including multiple extruders arranged in a cascaded fashion with the material passing continuously from one extruder to the next.

Figure 2:
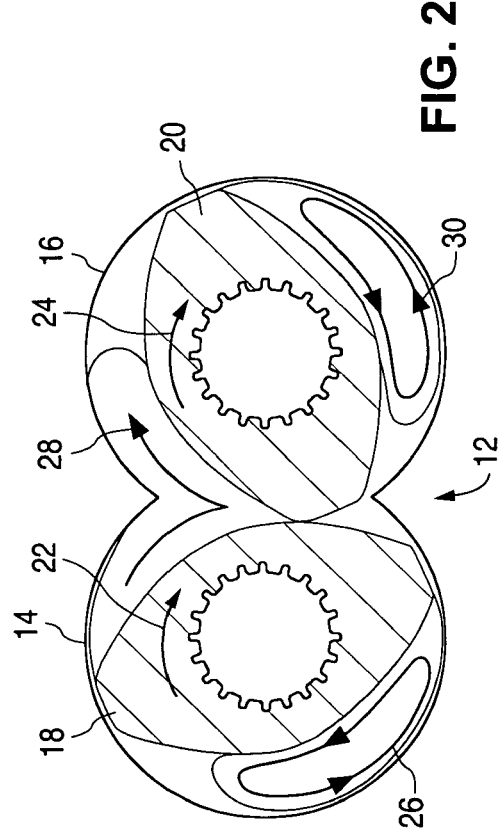
FIG. 2 is a cross-section of the twin screw extruder along the line 2-2 in FIG. 1.

Twin screw extruder 10 can include a longitudinal chamber 12. Referring to FIG. 2, chamber 12 has a pair of central cylinders 14 and 16 which house a pair of corresponding co-rotating twin extrusion screws 18 and 20, respectively. Each screw 18 and 20 can be mounted on a shaft that is integrated with a gear box housed by a motor 21. As indicated by arrows 22 and 24, each screw 18 and 20 can be configured to rotate within chamber 12 to convey the polymer in chamber 12. Arrows 26, 28 and 30 show the polymer flow within chamber 12 as the polymer is conveyed along twin screw extruder 10.

The configuration of the twin screws 18 and 20 can be any suitable configuration that allows the twin screws to mix the material introduced into twin screw extruder 10, and convey the material through extruder 10. In one embodiment, the configuration illustrated in FIG. 3, as further described in Example 1, is used.

Twin screw extruder 10 can have a multiple number of barrels which act as discrete mixing zones. The barrels can have a total length to diameter ratio in the range of about 32-52, and more narrowly, about 36-44. In each of these mixing zones or barrels, the shear rate, shear stress, energy flux, plastics material flow and temperature can be individually controlled. By controlling these particular process variables in each zone, the process of the present invention can effectively remove impurities from the polymer. Twin screw extruder 10 can have any suitable number of barrels for mixing the polymer. For example, twin screw extruder 10 can have one to fifteen barrels, more narrowly from eight to thirteen barrels. As illustrated in FIG. 1, twin screw extruder 10 has eight barrels marked 32A through 32H, including one "dummy barrel" (barrel 32A), and two double length barrels (barrels 32F and 32G). Each of the barrels can have a separate temperature control that can heat or cool the contents as needed.

The polymer can be introduced into twin screw extruder 10 by a feeder 34 into second barrel 32B. As noted above, first barrel 32A can act as a "dummy barrel." Representative examples of feeder 34 include a twin screw gravimetric feeder or a belt resin feeder. Representative feeders may be obtained from K-tron International, Inc. of Pitman, N.J. To realize greater process efficiency, the polymer can be introduced into the process by means of individually metered, continuous mass flow streams through feeder 34.

Twin screw extruder 10 can be in communication with a gas source 36. Gas source 36 can be used to deliver or introduce a gas that is capable of reducing the amount of degradation experienced by the polymer during the purification process. By way of example, gas source 36 can be in communication with second barrel 32B.

Figure 3:
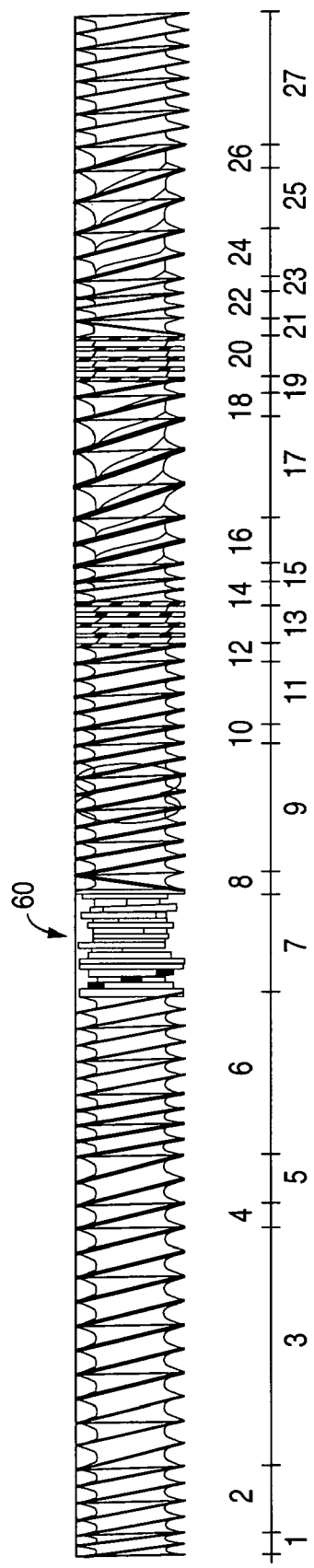
FIG. 3 is a side view of a twin screw configuration as referred to in the Example.

Once the polymer is introduced into twin screw extruder 10, the polymer is conveyed from one end to the other by twin screws 18 and 20. As the polymer is conveyed, the polymer should be in a liquid form. The polymer can be exposed to a temperature that decreases the viscosity of the polymer. The polymer can be heated at any point along the length of twin screw extruder 10, for example, at second and third barrels 32B and 32C. Furthermore, the viscosity of the polymer can be decreased by mechanical means, such as by kneading blocks that are housed in one or more barrels such as kneading block 60, as illustrated in FIG. 3.

The fluid that is capable of stripping or removing the impurity from the polymer can be introduced into twin screw extruder 10 at any point along chamber 12. Referring to FIG. 1, by way of example, the fluid can be introduced into twin screw extruder 10 through a first injection port 38 integrated with sixth barrel 32F and a second injection port 40 integrated with seventh barrel 32G of twin screw extruder 10. Different fluids, or the same fluids at different rates, can be directed into first injection port 38 and second injection port 40, respectively.

Twin screw extruder 10 can be constructed so that the pressure in chamber 12 is sufficiently low at the point where the fluid in injected so that the fluid can be injected into chamber 12 without being ejected or blown-out from chamber 12. For instance, the screw configuration of twin screw extruder 10 can be arranged so that there is a rotational orientation along sixth and seventh barrels 32F and 32G that reduces the pressure in chamber 12 at these points to about atmospheric pressure.

In one embodiment, a first fluid pump 42 is in communication with first injection port 38, and a second fluid pump 44 is in communication with second injection port 40. First and second fluid pumps 42 and 44 can be configured to provide measured pressure to meet a selected injection rate. A representative example of a pump that can be used for first and second pumps 42 and 44 is a piston pump available from American LEWA, Inc., Holliston, Mass.

After the fluid has captured the impurity and is in a vapor form, the fluid containing the impurity can be removed from twin screw extruder 10. Twin screw extruder 10 can have a first extraction port 46 and a second extraction port 48. Extraction ports 46 and 48 can be positioned after the point in which the fluid has been introduced into twin screw extruder 10. In one embodiment, an extraction port is positioned in close proximity to an injection port in order to extract the fluid vapor before any additional amount of fluid is added to extruder 10. Having an extraction port in close proximity to the injection port can be useful because it may allow the user to remove the fluid before the fluid has an opportunity to react with or otherwise adversely interact with the polymer being purified. Referring to FIG. 1, extraction port 46 is integrated with sixth barrel 32F and extraction port 48 is integrated with seventh barrel 32G. In one embodiment, extraction ports 46 and 48 are in communication with a vacuum 50.

Chamber 12 can be configured so that the volume of chamber 12 incrementally increases along the length of chamber 12 so that the volume of chamber 12 matches the increase of material added to chamber 12 (e.g., the fluid). In other words, chamber 12 can be configured so that the volume of chamber 12 is in proportion to the volume of material introduced at each port so as to maintain a substantially constant mixing volume fill factor within chamber 12. Fill factors can vary in the range of 10-90% of the effective (i.e., open) volume of chamber 12, and more narrowly 10-30%, to accommodate specific requirements of temperature, viscosity, dispersion and production throughput. If extraction ports 46 and 48 are sufficiently close to first and second injection ports 38 and 40, then it may not be necessary to increase the volume of chamber 12 along the length of chamber 12 because most of the fluid introduced into chamber 12 will be removed before approaching a critical fill factor.

Twin screw extruder 10 can have a die head 52 that is used to collect the purified polymer. Die head 52 can be pressurized and can eject the purified polymer through a die plate as strands into a bath 54 for cooling the purified polymer strands. The bath should contain a cooled liquid (e.g., circulating cool water) that does not adversely interact with the polymer, or add impurities to the same. Once cooled, the purified polymer is post processed by an air knife 56 and a strand pelletizer 58 for cutting the purified polymer strands into a suitable size.

Method of Forming the Coating

Herein is disclosed a method and system of purifying polymers for use with implantable medical devices, such as a stent. The implantable medical device may be any suitable medical substrate that can be implanted in a human or veterinary patient. In the interests of brevity, a drug delivery stent including a polymeric coating is described below. However, one of ordinary skill in the art will understand that other medical substrates can be manufactured using the purified polymers produced by the present invention. For example, devices that are partially or completely made from purified bioabsorbable or biostable polymers can be constructed by using the embodiments of the present invention. Such devices include stents or polymeric sheaths that are fabricated by using the purified polymer.

Examples of implantable medical devices include self-expandable stents, balloon-expandable stents, stent-grafts, grafts (e.g., aortic grafts), artificial heart valves, cerebrospinal fluid shunts, pacemaker electrodes, and endocardial leads (e.g., FINELINE and ENDOTAK, available from Guidant Corporation, Santa Clara, Calif.). The underlying structure or substrate of a coated device can be polymeric, metallic, ceramic, or made from any suitable material and can be of virtually any design. The underlying structure of the device can be made of a metallic material or an alloy such as, but not limited to, cobalt chromium alloy (ELGILOY), stainless steel (316L), high nitrogen stainless steel, e.g., BIODUR 108, cobalt chrome alloy L-605, "MP35N," "MP20N," ELASTINITE (Nitinol), tantalum, nickel-titanium alloy, platinum-iridium alloy, gold, magnesium, or combinations thereof. "MP35N" and "MP20N" are trade names for alloys of cobalt, nickel, chromium and molybdenum available from Standard Press Steel Co., Jenkintown, Pa. "MP35N" consists of 35% cobalt, 35% nickel, 20% chromium, and 10% molybdenum. "MP20N" consists of 50% cobalt, 20% nickel, 20% chromium, and 10% molybdenum. As noted above, the device can also be made partially or completely from a purified bioabsorbable or biostable polymer.

After the polymer has been purified, the polymer can be applied to a stent to form a coating that is substantially biologically inert. "Purified" refers to a polymer that has had impurities removed or significantly reduced. "Impurities" refer to traces of catalysts, initiators, processing aids, suspension aids, unreacted monomers and oligomers, or other low molecular weight species, or any other chemical remaining in the polymer, that can cause or effectuate an adverse biological response greater than which would occur if the impurity is removed or significantly reduced. For example, "food packaging grade" EVAL can contain impurities such as unreacted and partially reacted monomers, synthesis agents (e.g., initiators, suspension agents, etc.) and by-products such as sodium hydroxide and sodium acetate, and lower molecular weight oligomers. "Biologically inert" refers to a material that does not elicit a significantly greater adverse biological response than a biocompatible material, such as stainless steel, when implanted into a body vessel.

To fabricate the coating, the purified polymer, or a blend of purified polymers, can be applied on the stent using commonly used techniques known to those having ordinary skill in the art. For example, the polymer can be applied to the stent by dissolving the polymer in a coating solvent, or a mixture of solvents, and applying the resulting solution on the stent by spraying or immersing the stent in the solution.

Representative examples of some suitable coating solvents include chloroform, acetone, water (buffered saline), dimethylsulfoxide, propylene glycol methyl ether, iso-propylalcohol, n-propylalcohol, methanol, ethanol, tetrahydrofuran, dimethylformamide, dimethylacetamide, benzene, toluene, xylene, hexane, cyclohexane, pentane, heptane, octane, nonane, decane, decalin, ethyl acetate, butyl acetate, isobutyl acetate, isopropyl acetate, butanol, diacetone alcohol, benzyl alcohol, 2-butanone, cyclohexanone, dioxane, methylene chloride, carbon tetrachloride, tetrachloroethylene, tetrachloro ethane, chlorobenzene, 1,1,1-trichloroethane, formamide, hexafluoroisopropanol, 1,1,1-trifluoroethanol, and hexamethyl phosphoramide and a combination thereof.

The purified polymer can also be combined with an active agent. The active agent or drug can include any substance capable of exerting a therapeutic or prophylactic effect for a patient. The drug may include small molecule drugs, peptides, proteins, oligonucleotides, and the like. The active agent could be selected, for example, to inhibit the activity of vascular smooth muscle cells. It can be directed at inhibiting abnormal or inappropriate migration and/or proliferation of smooth muscle cells to inhibit restenosis. Examples of drugs include immunosuppressive substances such as rapamycin and structural derivatives or functional analogs thereof, such as 40-O-(2-hydroxy)ethyl-rapamycin (known by the trade name of Everolimus available from Novartis), 40-O-tetrazole-rapamycin, 40-O-(3-hydroxy)propyl-rapamycin and 40-O-[2-(2-hydroxy)ethoxy]ethyl-rapamycin; and antiproliferative substances such as actinomycin D, or derivatives and analogs thereof. Synonyms of actinomycin D include dactinomycin, actinomycin IV, actinomycin $I_1$, actinomycin $X_1$, and actinomycin $C_1$. The active agent can also fall under the genus of antineoplastic, anti-inflammatory, antiplatelet, anticoagulant, antifibrin, antithrombin, antimitotic, antibiotic, antiallergic, and antioxidant substances. Examples of such antineoplastics and/or antimitotics include paclitaxel, docetaxel, methotrexate, azathioprine, vincristine, vinblastine, fluorouracil, doxorubicin, hydrochloride, and mitomycin. Examples of such antiplatelets, anticoagulants, antifibrin, and antithrombins include sodium heparin, low molecular weight heparins, heparinoids, hirudin, argatroban, forskolin, vapiprost, prostacyclin and prostacyclin analogues, dextran, D-phe-pro-arg-chloromethylketone (synthetic antithrombin), dipyridamole, glycoprotein IIb/IIIa platelet membrane receptor antagonist antibody, recombinant hirudin, and thrombin. Examples of such cytostatic or antiproliferative agents include angiopeptin, angiotensin converting enzyme inhibitors such as captopril, cilazapril or lisinopril, calcium channel blockers (such as nifedipine), colchicine, fibroblast growth factor (FGF) antagonists, fish oil (ω-3-fatty acid), histamine antagonists, lovastatin (an inhibitor of HMG-CoA reductase, a cholesterol lowering drug), monoclonal antibodies (such as those specific for Platelet-Derived Growth Factor (PDGF) receptors), nitroprusside, phosphodiesterase inhibitors, prostaglandin inhibitors, suramin, serotonin blockers, steroids, thioprotease inhibitors, triazolopyrimidine (a PDGF antagonist), and nitric oxide. An example of an antiallergic agent is permirolast potassium. Other therapeutic substances or agents which may be appropriate include alpha-interferon; genetically engineered epithelial cells; tacrolimus; and dexamethasone.

In an embodiment of the present invention, a stent has a coating that includes a purified polymer and a drug. The polymer can be purified by methods detailed herein. The stent can be used for implantation at a selected region of a vessel of a patient for treating of, preventing, or delaying the onset of restenosis or vulnerable plaque, and can include an active agent.

The coating for a stent including the purified polymer can have a drug-polymer layer, an optional topcoat layer, and an optional primer layer. The drug-polymer layer can be applied directly onto the stent surface to serve as a reservoir for a therapeutically active agent or drug which is incorporated into the drug-polymer layer. The topcoat layer, which can be essentially free from any therapeutic substances or drugs, serves as a rate limiting membrane for controlling the rate of release of the drug. The optional primer layer can be applied between the stent and the drug-polymer layer to improve the adhesion of the drug-polymer layer to the stent.

After purification, the polymers can be used for making either the drug-polymer layer, the topcoat membrane, the optional primer layer, or any combination thereof.

Method of Making a Drug-Delivery Implantable Medical Device

The embodiments of the present invention additionally provide a method for making a composition for manufacturing a drug-delivery implantable medical device, such as a drug-delivery or eluting stent. The composition may be a polymer mixture that includes a polymer and active agent. The polymer mixture may be used as a coating for an implantable medical device. Alternatively, an implantable medical device may be fabricated from the polymer mixture. Whether a polymer mixture is used to coat or form an implantable medical device, the ratio of polymer to active agent and the homogeneity of the polymer mixture are important parameters in treating a diseased site in a vessel.

An advantage of the present invention over previous methods is that a homogeneous or substantially homogeneous mixture of polymer and active agent is produced. The method employs a mixing apparatus that may subject a material to intense mixing in a short duration. Consequently, a coating may be applied to an implantable medical device that is also homogeneous or substantially homogeneous, both parallel to the plane of the coating as well as across the thickness of the coating. In addition to the intense degree of mixing, despite the intense degree of mixing, the method can include controlling the temperature within the apparatus to prevent degradation of the active agent.

Another advantage of the present invention is that the entire process of manufacturing an implantable medical device may be performed in one set of apparatuses. For example, a commercial polymer may be fed into a first apparatus, such as an extruder. The polymer may then be purified and then combined with an active agent and a solvent to form a composition for coating an implantable medical device. The composition may then be fed into a second apparatus, such as an injection molder, to coat an implantable medical device.

In one embodiment, the method may include introducing a polymer into a mixing apparatus. Representative examples of polymers are given above. In one embodiment, the mixing apparatus may include an extruder. Representative examples of extruders are disclosed above. Mixing a composition with an extruder is particularly advantageous since an extruder can perform a much more intense agitation to a composition in a shorter period of time than agitation techniques conventionally employed. The method may further include introducing an active agent and a solvent into the apparatus. In some embodiments, the polymer may be purified in the apparatus, as described above, prior to mixing the polymer with the active agent and the solvent. Alternatively, the polymer introduced into the apparatus may not require purification. The method may then include mixing the active agent with the polymer in the apparatus to produce a polymer mixture. The method may also include mixing the solvent with the polymer in the apparatus. In certain embodiments, the temperature of the polymer mixture may be controlled in at least a portion of the apparatus. The polymer mixture may then be removed from the apparatus. The removed polymer mixture may be used as a coating on an implantable medical device, or for fabricating an implantable medical device.

In some embodiments, the solvent may be a mutual solvent for the polymer and the active agent. Thus, the solvent may be capable of dissolving at least a portion of the polymer and at least a portion of the active agent. In some embodiments, at least a portion of the polymer mixture may be a homogeneous or substantially homogenous mixture at the molecular- or ionic-size level of polymer, active agent, and solvent. In other embodiments, all or substantially all of the polymer mixture may be a homogeneous or substantially homogenous mixture at the molecular- or ionic-size level of polymer, active agent, and solvent. Representative solvents have been provided above.

As described above, a polymer with or without an impurity may be introduced into a mixing apparatus in a solid form or a melted form. The polymer may be heated prior to introduction to melt the polymer or heated subsequent to introduction in the mixing apparatus. If it is desirable to purify the polymer, the mixing apparatus may be configured to purify the polymer, as described above. Purification may be performed in the mixing apparatus prior to forming the polymer mixture that contains a polymer and active agent. Alternatively, if purification is not desired, the mixing apparatus may be configured to form the polymer mixture without first purifying the polymer. As the polymer is introduced into the mixing device, or any time during the purification and/or process for making the polymer mixture, a gas may be delivered to the mixing apparatus to reduce the amount of degradation or discoloration experienced by the polymer and degradation of the active agent. For example, the gas can remove atmospheric oxygen from the mixing apparatus. Therefore, the polymer may be mixed in an inert or substantially inert atmosphere. Representative examples of gases that can be delivered include inert gases such as nitrogen, argon, etc. In addition, the condition of the polymer as it is mixed in the apparatus may be substantially as described above.

The next stages of the method may include introducing active agent and optionally solvent into the apparatus. Representative examples of active agents and solvent are described above. The method may include alternative embodiments of introducing the active agent and solvent into the mixing apparatus. In one embodiment, the active agent may be introduced or fed as a solid, for example as particles or powder. Representative feed rates of the active agent in solid form may be from up to about 5 gm/min, and more narrowly up to about 1.5 gm/min. In this embodiment, a pure solvent may be introduced or injected into the apparatus in addition to the solid active agent. Representative injection rates of the solvent may be up to about 500 gm/min, and more narrowly about 50 gm/min to about 200 gm/min. As used herein, a "pure solvent" refers to a solvent that is free or substantially free of active agent or other impurities. Alternatively, the active agent and solvent may be introduced into the apparatus contemporaneously as a fluid mixture or solution. Consequently, the active agent and the solvent may be mixed contemporaneously with the polymer.

In another embodiment of the method, a pure solvent and the solvent-active agent mixture may be introduced into the apparatus. The method may also include introducing the active agent as a solid and introducing the solvent-active agent mixture into the apparatus. In addition, an embodiment may include introducing the active agent as a solid, introducing the pure solvent, and introducing the solvent-active agent mixture into the apparatus. Regardless of the method of introducing the active agent, the polymer and active agent may be combined in the apparatus to form a polymer mixture that is homogeneous or substantially homogeneous in at least a portion of the apparatus.

As discussed above, the ratio of the active agent to polymer may be an important treatment parameter of an implantable medical device. It may be desirable for the ratio to be within a particular range or near or at a selected value. For example, a typical ratio of an active agent to polymer ratio may be between about 1:3 to about 1:5. Some embodiments of the method may include controlling the ratio of active agent to polymer in the polymer mixture in a least a portion of the apparatus. The method may employ at least one of several embodiments for controlling the ratio of polymer to active agent. In one embodiment, the introduction or feed rate of solid active agent may be controlled to obtain a desire range or value of the ratio. In this case, the feed rate of active agent may be increased to increase the ratio. In another embodiment, a desired range or value of the ratio may be obtained by controlling the introduction, or flow-rate, of the solvent-active agent mixture into the apparatus. The injection rate of the solvent-active agent mixture may be increased to increase the ratio.

In certain embodiments, a closed loop feedback system may be used to facilitate the control of the ratio of active agent to polymer in the polymer mixture. A "closed-loop feedback system" refers to an automatic control system for an operation or process in which feedback in a closed path or group of paths maintains output at a desired level. For example, the feedback may be the active agent to polymer ratio at a selected location in the mixing apparatus. The ratio at the selected location may be monitored by a sensor disposed within the apparatus. The sensor may then transmit a ratio signal to a computer system configured to operate as a control system. The control system may then determine a control signal adapted to respond to the measured ratio. The control signal may be, for example, an instruction for a feeder to increase or decrease the feed rate of solid active agent or an instruction for a pump to increase or decrease the injection rate of the solvent-active agent mixture. The control signal may then be transmitted to the feeder, which may respond to the control signal with an instruction for a solid active agent feeder to increase or decrease the feed rate of the solid active agent to the apparatus. Similarly, the control signal may then be transmitted to a pump, which may respond to the control signal by increasing or decreasing an injection rate of solvent-active agent mixture into the apparatus.

Other embodiments of obtaining a desired range or value of the active agent to polymer ratio may include combinations of the above embodiments. These combinations include: controlling the feed rate of solid active agent and the injection rate of pure solvent; controlling the injection rate of the pure solvent and solvent-active agent mixture; controlling the feed rate of the solid active agent and solvent-active agent mixture; and controlling the injection rate of the solid active agent, the pure solvent, and solvent-active agent mixture.

Furthermore, it may be advantageous to control the viscosity of the polymer mixture through variation of injection rates of the solvent and/or solvent-active agent mixture. The desired viscosity depends on the intended use of the polymer mixture. If the polymer mixture is to be used to coat an implantable medical device, a relatively low, water-like viscosity is desirable. However, a viscosity similar to a polymer melt is more desirable for the polymer mixture if it is to be used in fabricating an implantable medical device. In one embodiment, the introduction or injection rate of the solvent may be controlled to obtain a desired viscosity. In another embodiment, the introduction or injection rate of the solvent-active agent mixture may be controlled to obtain a desired viscosity of the polymer. Alternatively, both the injection rates of the solvent and solvent-active agent mixture may be controlled. In some embodiments, the control of the viscosity may be facilitated by a closed loop control system in a manner similar to that described for controlling the active agent to polymer ratio.

Furthermore, controlling the temperature of the polymer mixture during the mixing process is important in preventing degradation of the active agent. The temperature of the polymer mixture may be controlled to be below a degradation temperature or degradation temperature range. For example, some active agents tend to degrade at temperatures above about 80° C. Others may tend to degrade above about 100° C. In one embodiment, the temperature of the polymer mixture may be controlled by controlling the introduction or injection rate of the solvent and/or solvent-active agent mixture to achieve a desired temperature range of the polymer mixture in at least a portion of the apparatus. Increasing the flow rate of solvent and/or solvent-active agent mixture may control the temperature since the increased flow rate tends to decrease the viscosity of the polymer mixture in at least a portion of the apparatus. As the viscosity decreases, the intensity of mixing necessary to achieve a desired degree of mixing decreases. Therefore, less work may be done on the polymer mixture by the apparatus. Consequently, less heat energy due to friction from the mixing process may be transferred to the polymer mixture.

In addition, changing the flow rate of solvent and/or solvent-active agent mixture changes the proportion of fluid in the apparatus that may be at a different temperature than the polymer mixture, which may further control the temperature in the apparatus. In some embodiments, the solvent and/or solvent-active agent mixture may be cooled to a temperature below an ambient temperature prior to introduction into the apparatus. In other embodiments, the solvent and/or solvent-active agent mixture may be heated to a temperature above an ambient temperature prior to introduction into the apparatus. In other embodiments, the temperature of the polymer mixture in the apparatus may be controlled with a heat exchanger in the apparatus. The resulting heat transfer may result in a decrease in temperature. In some embodiments, the temperature may be controlled by a heat exchanger and the injection rate of the solvent and/or solvent-active agent mixture.

Another advantage of present method may be that it allows intense mixing of the active agent with the polymer below a degradation temperature range. In order to mix some polymers and an active agent without the addition of fluid such as solvent and/or solvent-active agent mixture, it may be necessary to mix above a degradation temperature range. Some polymers may harden or freeze below a degradation temperature range. For example, if the temperature of the extruder is controlled to below a degradation temperature range by a heat exchanger in a mixing apparatus, some polymers may harden or freeze. For example, crystalline polymers with melting temperatures near or above a degradation temperature range may freeze and amorphous polymers with melting temperatures near or above a degradation temperature range may harden. Therefore, mixing such polymers near or below a degradation temperature range may be difficult or impossible.

Additionally, the degradation of active agents may depend on both the temperature and time of exposure to a temperature range. Even if a temperature is within "safe zone," a prolonged exposure of the active agent to an elevated temperature may have adverse effects on the agent. Therefore, it may be desirable to limit the time that an active agent is within a mixing apparatus or its residence time. The process parameters may be configured to limit the residence time of the polymer mixture in the extruder to a time less than a time that results in a minimum acceptable degradation of the active agent. In an embodiment, the residence time may be influenced by the extruder screw configuration and the rotation speed of the screw. In one embodiment, the residence time in the apparatus may be less than about 10 seconds, or less than about 7 seconds. In addition, even if the temperature is greater than or equal to a degradation temperature range, degradation of the active agent may be inhibited or prevented by a low enough residence time. For example, in some embodiments, a temperature in a portion of the apparatus may be between about 60° C. and about 240° C. without significant degradation of active agent with a sufficiently low residence time.

In one embodiment, a closed loop feedback system may be used to facilitate the control of the temperature of polymer mixture in the apparatus. For example, the feedback may be the temperature at a selected location in the mixing apparatus. The temperature at the selected location may be monitored by a thermocouple disposed within the apparatus. The sensor may then transmit a temperature signal to a computer system configured to operate as a control system. The control system may then determine a control signal adapted to respond to the measured temperature. The control signal may be, for example, an instruction for a pump to increase or decrease the injection rate of the solvent to the apparatus. The control signal may then be transmitted to a pump, which may respond to the control signal by increasing or decreasing an injection rate of solvent. Alternatively, the control signal may be transmitted to a cooling system within the apparatus.

An embodiment of the method further includes removing the polymer mixture from the apparatus. The polymer mixture may have suitable properties including but not limited to homogeneity, viscosity, and/or active agent to polymer ratio for a selected application. The polymer mixture may be used for coating an implantable medical device or fabricating an implantable medical device. For example, the polymer mixture may be fed to an injection molding apparatus which may form a coating on the implantable medical device. Alternatively, the implantable medical device may be coated by spraying the polymer mixture on to an implantable medical device. In addition, an implantable medical device may be fabricated with the polymer mixture. One embodiment may include feeding the removed polymer mixture to an injection molding apparatus, forming a tube or sheath. The tube may be disposed over an uncoated implantable medical device. Alternatively, a pattern that includes a network of interconnecting elements or struts may be formed on the surface of the tube using a laser cutting technique, for example.

In some embodiments, the polymer mixture in the apparatus may include a solvent. It may be desirable to remove at least some of the solvent from the polymer mixture prior to removing the polymer mixture from the apparatus. Any method for removing solvent should limit or prevent exposure of the polymer mixture to a temperature range that may degrade the active agent. The polymer mixture may be heated to a temperature equal to or greater than the boiling point of the solvent at ambient pressure. An alternative method for removing solvent may be more desirable if heating the polymer mixture to such temperatures would expose the polymer mixture to a temperature range that may degrade the active agent. Alternatively, a solvent may be used with a boiling point at ambient pressure below a temperature that may degrade an active agent. At least some solvent in vapor form may then be removed from the mixing apparatus. The solvent in the polymer mixture may be allowed to evaporate from the mixing apparatus under 1 atm, or the solvent may be extracted under a vacuum or reduced pressure, for example, a pressure less than less than about 300 mm Hg, or more narrowly, less than about 10 mm Hg.

In another embodiment, at least some solvent may be removed from the polymer mixture after removal from the mixing apparatus. For example, solvent may be removed from the polymer mixture in vapor form during an injection molding process. Alternatively, the polymer mixture may be subjected to a heat treatment after removal from the mixing apparatus and prior to coating or fabrication of an implantable medical device. The heat treatment may be performed in a temperature range and with a duration that will cause less than a minimally acceptable degradation of the active agent. For example, the heat treatment may be conducted between about 30° C. to about 60° C. for between 15 minutes and about 4 hours. The heating may be conducted in an anhydrous atmosphere and at an ambient pressure. The heating may, alternatively, be conducted under vacuum condition.

System for Making a Drug-Eluting and/or Delivery Implantable Medical Device

Figure 4:
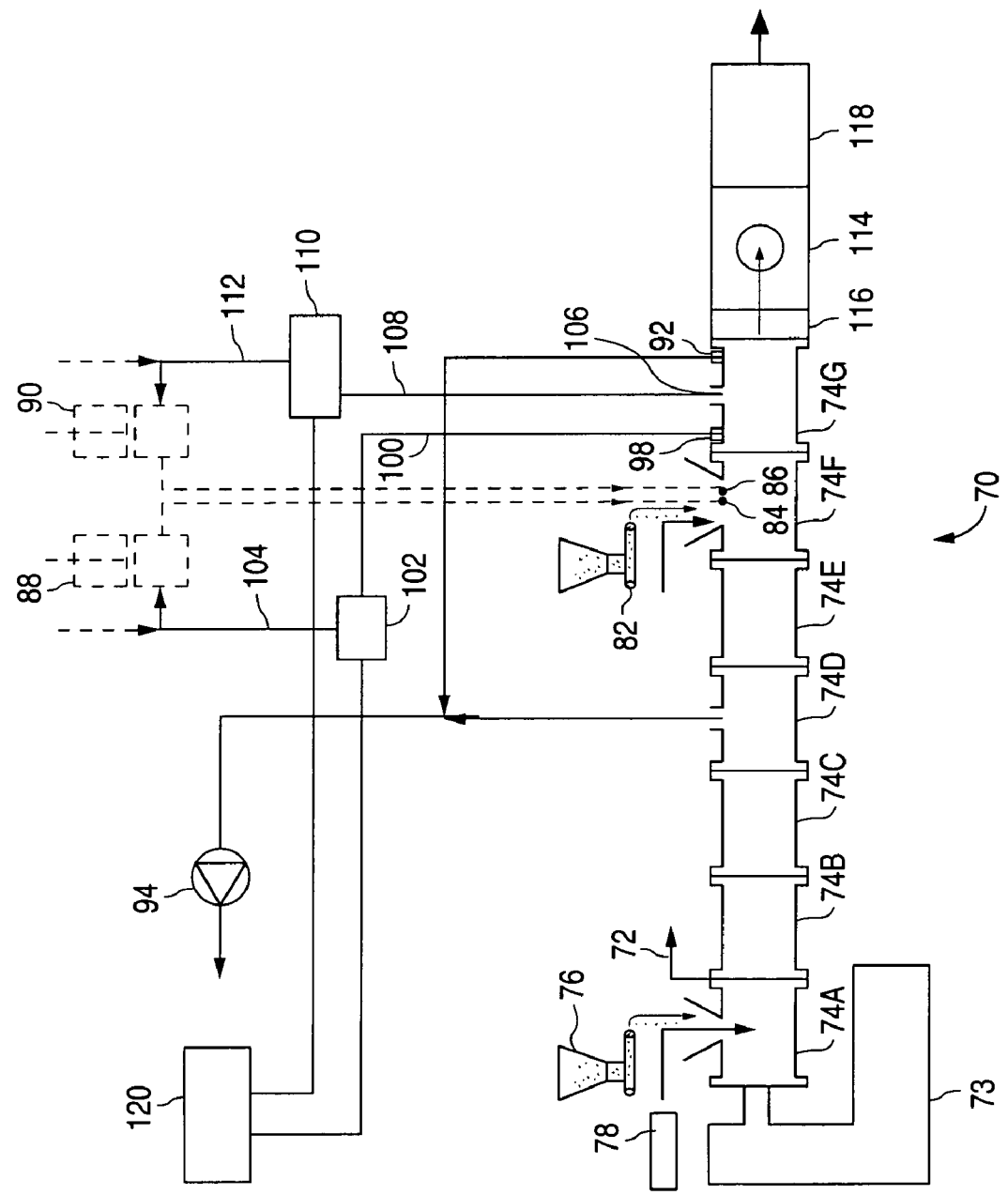
FIG. 4 is an illustration of a system including a twin screw extruder for coating or fabricating an implantable medical device in accordance with an embodiment of the present invention.

FIG. 4 illustrates a system configured to manufacture a drug-delivery implantable medical device. FIG. 4 includes an illustration of an example of a twin screw extruder 70 which has some attributes similar to twin screw extruder 10 in FIG. 1. Twin screw extruder 70 is configured for making a composition for manufacturing an implantable medical device. Another configuration may include a first section configured to purify the polymer as shown in FIG. 1 and a second section configured as in FIG. 4. The configuration illustrated in FIG. 4 is an intermeshing co-rotating twin screw extruder. However, other configurations for a twin screw extruder are contemplated as useful with the process of making a composition for manufacturing an implantable medical device.

Twin screw extruder 70 can include a longitudinal chamber 72. The internal configuration of twin screw extruder 70 may be similar to that illustrated in FIG. 2. The configuration of the twin screws can be any suitable configuration that allows the twin screws to mix the material introduced into twin screw extruder 70, and convey the material through extruder 70. Motor 73 is configured to rotate the twin screws to convey the polymer and the polymer mixture in chamber 72. In one embodiment, the configuration illustrated in FIG. 3, as further described in Example 1, is used.

Twin screw extruder 70 can have a multiple number of barrels which act as discrete mixing zones. The barrels can have a total length to diameter ratio in the range of about 32-52, and more narrowly, about 36-44. In each of these mixing zones or barrels, the shear rate, shear stress, energy flux, plastics material flow, and temperature can be individually controlled. By controlling these particular process variables in each zone, the process of the present invention can effectively mix a polymer with an active agent and a solvent. Twin screw extruder 70 can have any suitable number of barrels for mixing the polymer, active agent, and solvent. For example, twin screw extruder 70 can have one to fifteen barrels, more narrowly from eight to thirteen barrels. As illustrated in FIG. 4, twin screw extruder 70 has seven barrels marked 74A through 74G. Each of the barrels can have a separate temperature control that can heat or cool the contents as needed. This is particularly important for preventing degradation of the drug.

The polymer can be introduced into twin screw extruder 70 by a feeder 76 into first barrel 74A. Representative examples of feeder 76 include a twin screw gravimetric feeder or a belt resin feeder. To realize greater process efficiency, the polymer can be introduced into the process by means of individually metered, continuous mass flow streams through feeder 76.

Twin screw extruder 70 can be in communication with a gas source 78. Gas source 78 can be used to deliver or introduce a gas that is capable of reducing the amount of degradation experienced by the polymer and active agent during the process for making the polymer mixture. By way of example, gas source 78 can be in communication with first barrel 74A. Also, by way of example, vacuum pump 94 can be in communication with barrel 74D.

Once the polymer is introduced into twin screw extruder 70, the polymer is conveyed from one end to the other by twin screws 18 and 20, as shown in FIG. 2. As the polymer is conveyed, the polymer should be in a liquid form. The polymer can be exposed to a temperature that decreases the viscosity of the polymer. The polymer can be heated at any point along the length of twin screw extruder 70, for example, at second and third barrels 74B and 74C. Furthermore, the viscosity of the polymer can be decreased by mechanical means, such as by kneading blocks that are housed in one or more barrels such as kneading block 60, as illustrated in FIG. 3.

The active agent can be introduced into twin screw extruder 70 at any point along chamber 72. Referring to FIG. 4, by way of example, the active drug can be introduced into twin screw extruder 70 by a feeder 82 into sixth barrel 74F. The pure solvent can be introduced into twin screw extruder 70 at any point along chamber 72. Referring to FIG. 4, by way of example, the pure solvent can be introduced into twin screw extruder 70 through a first injection port 84 integrated with sixth barrel 74F. The solvent-active agent mixture can be introduced into twin screw extruder 70 at any point along chamber 72. Referring to FIG. 4, by way of example, the solvent-active agent mixture can be introduced into twin screw extruder 70 through a second injection port 86 integrated with sixth barrel 74F.

Twin screw extruder 70 can be constructed so that the pressure in chamber 72 is sufficiently low at the point where the solvent and/or solvent-active agent mixture is injected so that the fluid can be injected into chamber 72 without being ejected or blown-out from chamber 72. For instance, the screw configuration of twin screw extruder 70 can be arranged so that there is a rotational orientation along sixth and seventh barrels 74F and 74G that reduces the pressure in chamber 72 at these points to about atmospheric pressure.

In one embodiment, a first pump 88 is in communication with first injection port 84, and a second pump 90 is in communication with second injection port 86. First and second fluid pumps 88 and 90 can be configured to provide measured pressure to meet a selected injection rate. A representative example of a pump that can be used for first and second pumps 88 and 90 is a piston pump available from American LEWA, Inc., Holliston, Mass.

The polymer can be mixed homogeneously with any one or any combination of the solid active agents, the pure solvent, and the solvent-active agent mixture at any point after entering chamber 72. As illustrated in FIG. 4, the polymer, the solid active agent, the pure solvent, and/or the solvent-active agent mixture are mixed in barrels 74F and 74G.

At any point after injection of the pure solvent and/or solvent-active agent mixture, a portion of the solvent in vapor form can be removed from twin screw extruder 70. Twin screw extruder 10 can have an extraction port 92. An extraction port 92 can be positioned after the point in which the pure solvent and/or solvent-active agent mixture has been introduced into twin screw extruder 70. Referring to FIG. 4, by way of example, an extraction port is positioned in 74G. In one embodiment, extraction port 92 is in communication with vacuum 94.

Chamber 72 can be configured so that the volume of chamber 72 incrementally increases along the length of chamber 72 so that the volume of chamber 72 matches the increase of material added to chamber 72 (i.e., the solvent and the active agent). In other words, chamber 72 can be configured so that the volume of chamber 72 is in proportion to the volume of material introduced at each port so as to maintain a substantially constant mixing volume fill factor within chamber 72. Fill factors can vary in the range of 10-90% of the effective (i.e., open) volume of chamber 72, and more narrowly 10-30%, to accommodate specific requirements of temperature, viscosity, dispersion, and production throughput.

Twin screw extruder 70 can have closed loop control systems to control the polymer active agent ratio and the temperature in twin screw extruder 70. A closed loop control system for the temperature can include any number of thermocouples disposed at any location along chamber 72. By way of example, as shown in FIG. 4, thermocouple 98 is disposed within chamber 72. Thermocouple 98 measures a temperature and transmits a temperature signal 100 to a control system 102. Control system 102 determines an appropriate feedback response to temperature signal 100. A control signal 104 is then transmitted to pump 88 which is adapted to respond to control signal 104 by increasing or decreasing the injection rate of solvent. A computer workstation 120 for monitoring conditions in extruder 70 and for manual control is communicatively coupled to control system 102.

A closed loop control system for the active agent to polymer ratio can include any number of composition sensors disposed at any location along chamber 72. By way of example, as shown in FIG. 4, sensor 106 is disposed within chamber 72. Sensor 106 measures an active agent to polymer ratio and transmits a ratio signal 108 to a control system 110. The composition may be determined from a viscosity measured by a rheometer. Control system 110 determines an appropriate feedback response to ratio signal 108. A control signal 112 is then transmitted to pump 90 which is adapted to respond to control signal 112 by increasing or decreasing the injection rate of solvent-active agent mixture. Computer workstation 120 is communicatively coupled to control system 110. A control system can also be communicatively coupled to feeder 82.

Twin screw extruder 70 can have a die head 114 that is used to collect the polymer mixture. An adapter plate 116 is configured to connect die head 114 to twin screw extruder 70. Die head 114 can be pressurized and can eject the polymer mixture for use in coating or fabricating an implantable medical device. By way of example, as shown in FIG. 4, die head 114 feeds an injection molder 118 which coats an implantable medical device with the polymer mixture.

Example 1

Some embodiments of the present invention are illustrated by the following Example. The Example is being given by way of illustration only and not by way of limitation. The Example illustrates the method of purification of the polymer. The parameters and data are not be construed to unduly limit the scope of the embodiments of the invention.

EVAL was purified using a purification system including a modified ZSK-25 mm twin screw extruder (available from Coperion Holding GmbH, Stuttgart, Germany). The system was used to perform twenty-six separate runs, each having different parameters as summarized below. The EVAL was supplied by the EVAL Company of America, Houston, Tex. Three different lots of EVAL were purified using the system: Lot 1 (manufacturer lot number LOST 31); Lot 2 (manufacturer lot number LIUB 33) and Lot 3 (manufacturer lot number LUJK 52).

The purification system used for this Example is illustrated in FIG. 1, and included a gravimetric loss-in-weight feeder for feeding the resin, two piston pumps for injecting stripping fluids, and two vent or extraction ports. The total processing barrel length was L/D=40, excluding one "dummy barrel." Each barrel was equipped with its own independent heating and cooling system.

As illustrated in FIG. 1, EVAL pellets were introduced at a feed throat at second barrel 32B of the extruder. First barrel 32A acted as a "dummy barrel." Nitrogen was bled at second barrel 32B to minimize the degradation of the melted EVAL resin. The feed throat was water-cooled. The EVAL resin was then heated in third barrel 32C, and melted and homogenized in fourth and fifth barrels 32D and 32E.

The fluids were injected into sixth and seventh barrels 32F and 32G with calibrated piston pumps. Four different fluids were used in separate runs: water, a mixture of isopropyl alcohol and water (65/35 by w/w), ethanol and DMSO. The ratio of fluid to resin was about 0.14-0.37 lbs. of fluid for every pound of EVAL resin.

A vacuum pump was connected to sixth and seventh barrels 32F and 32G. The purified polymer was pressurized in eighth barrel 32H and discharged through a die plate of die head 52 at a 45 degree angle to bath 54 having circulating cooled water. The strand was water cooled, air knifed and pelletized.

The screw configuration for the Example is illustrated in FIG. 3. The extruder's screw configuration was designed to provide sufficient shear rate and stress to melt the EVAL pellets. The following Table 2 provides a summary of the screw configuration. The "Element" column refers to segments of first screw 18 as illustrated in FIG. 3. Elements 13 and 20 correspond to the segments in which the fluid was injected into the extruder, whereas elements 17 and 25 correspond to the segments in which the fluid was extracted from the extruder.

The "Pitch" column refers to the ratio of width/length of first screw 18 expressed in millimeters. The width is the distance between the threads of first screw 18 and the length is the length of the corresponding segment.

TABLE 2

| ELEMENT | PITCH (mm) | DIRECTION OF ROTATION |
|---|---|---|
| 1 | 16/16 | Right-Handed |
| 2 | 24/24 | Right-Handed |
| 3 | 36/36 | Right-Handed |
| 4 | 36/18 | Right-Handed |
| 5 | 36/36 | Right-Handed |
| 6 | 24/24 | Right-Handed |
| 7 | Not Applicable (Kneading Block) | Not Applicable (Kneading Block) |
| 8 | 24/12 | Left-Handed |
| 9 | 24/24 | Right-Handed |
| 10 | 24/12 | Right-Handed |
| 11 | 24/24 | Right-Handed |
| 12 | 24/12 | Right-Handed |
| 13 | 8/16 | Right-Handed |

TABLE 2-continued

| ELEMENT | PITCH (mm) | DIRECTION OF ROTATION |
|---|---|---|
| 14 | 16/16 | Right-Handed |
| 15 | 24/12 | Right-Handed |
| 16 | 36/36 | Right-Handed |
| 17 | 48/24 | Right-Handed |
| 18 | 36/18 | Right-Handed |
| 19 | 24/12 | Right-Handed |
| 20 | 8/16 | Right-Handed |
| 21 | 24/12 | Left-Handed |
| 22 | 16/16 | Right-Handed |
| 23 | 24/12 | Right-Handed |
| 24 | 36/36 | Right-Handed |
| 25 | 48/24 | Right-Handed |
| 26 | 36/18 | Right-Handed |
| 27 | 24/24 | Right-Handed |

As noted above, the system was used to perform twenty-six separate runs. The run conditions are summarized in the following Table 3:

TABLE 3

Run Conditions

| | Sample # | | | | | | | |
|---|---|---|---|---|---|---|---|---|
| | 1 | 2 | 3 | 4 | 5 | 6 | 7 | 8 |
| Rotations/Minute Of Screws | 80 | 80 | 80 | 80 | 80 | 80 | 80 | 80 |
| Input Rate Of Polymer (lb/hr) | 7.5 | 7.5 | 7.5 | 7.5 | 7.5 | 7.5 | 7.5 | 7.5 |
| Torque Of Screws | 80 | 83 | 86 | 86 | 86 | 86 | 80 | 82 |
| Work On Material (kW) | 1.13 | 1.17 | 1.18 | 1.21 | 1.21 | 1.21 | 1.13 | 1.15 |
| EVAL Resin lot ID | 1 | 1 | 2 | 2 | 3 | 3 | 3 | 3 |
| Fluid | $H_2O$ | $H_2O$ | $H_2O$ | $H_2O$ | $H_2O$ | $H_2O$ | IPA/$H_2O$ | IPA/$H_2O$ |
| Injection Rate of Fluid (Barrel 32F) (ml/hr) | 0 | 675 | 0 | 580 | 0 | 570 | 0 | 520 |
| Injection Rate of Fluid (Barrel 32G) (ml/hr) | 525 | 525 | 500 | 500 | 490 | 490 | 540 | 540 |
| Number of Injections During Process | 1 | 2 | 1 | 2 | 1 | 2 | 1 | 2 |
| Vacuum Pressure (Barrel 32F) (mm Hg) | 2.0 | 4.5 | 1.5 | 5.8 | 2.5 | 7.0 | 2.4 | 6.2 |
| Vacuum Pressure (Barrel 32G) (mm Hg) | 6.5 | 5.5 | 4.5 | 6.3 | 5.8 | 7.2 | 4.4 | 6.2 |
| Temperature of Barrel 32C (° C.) | 190 | 190 | 190 | 190 | 190 | 190 | 190 | 190 |
| Temperature of Barrel 32D (° C.) | 190 | 190 | 190 | 190 | 190 | 190 | 190 | 190 |
| Temperature of Barrel 32E (° C.) | 180 | 180 | 180 | 180 | 180 | 180 | 180 | 182 |
| Temperature of Barrel 32F (° C.) | 170 | 170 | 170 | 170 | 170 | 170 | 170 | 172 |
| Temperature of Barrel 32G (° C.) | 170 | 170 | 170 | 170 | 170 | 170 | 170 | 170 |
| Temperature of Barrel 32H (° C.) | 170 | 170 | 170 | 170 | 170 | 170 | 170 | 170 |
| Temperature of Die Head (° C.) | 190 | 190 | 190 | 190 | 190 | 190 | 190 | 190 |
| Pressure of Chamber At Discharge (lb/in$^2$) | 186 | 225 | 209 | 240 | 190 | 220 | 235 | 231 |

| | Sample # | | | | | | | |
|---|---|---|---|---|---|---|---|---|
| | 9 | 10 | 11 | 12 | 13 | 14 | 15 | 16 |
| Rotations/Minute Of Screws | 80 | 80 | 80 | 80 | 80 | 80 | 80 | 80 |
| Input Rate Of Polymer (lb/hr) | 7.5 | 7.5 | 7.5 | 7.5 | 7.5 | 7.5 | 7.5 | 7.5 |
| Torque Of Screws | 82 | 87 | 82 | 80 | 78 | 80 | 78 | 79 |
| Work On Material (kW) | 1.15 | 1.22 | 1.15 | 1.13 | 1.10 | 1.13 | 1.10 | 1.11 |
| EVAL Resin lot ID | 2 | 2 | 1 | 1 | 1 | 1 | 2 | 2 |
| Fluid | IPA/$H_2O$ | IPA/$H_2O$ | IPA/$H_2O$ | IPA/$H_2O$ | ETOH | ETOH | ETOH | ETOH |
| Injection Rate of Fluid (Barrel 32F) (ml/hr) | 0 | 520 | 0 | 540 | 0 | 550 | 0 | 550 |
| Injection Rate of Fluid (Barrel 32G) (ml/hr) | 560 | 500 | 540 | 540 | 640 | 648 | 650 | 650 |
| Number of Injections During Process | 1 | 2 | 1 | 2 | 1 | 2 | 1 | 2 |

TABLE 3-continued

| Run Conditions | | | | | | | | |
|---|---|---|---|---|---|---|---|---|
| Vacuum Pressure (Barrel 32F) (mm Hg) | N/A | 7.2 | 4.0 | 6.0 | 6.0 | 7.5 | 7.0 | 8.5 |
| Vacuum Pressure (Barrel 32G) (mm Hg) | 7.2 | 7.2 | 5.0 | 6.0 | 6.5 | 7.0 | N/A | 9.0 |
| Temperature of Barrel 32C (° C.) | 190 | 190 | 190 | 190 | 196 | 190 | 191 | 190 |
| Temperature of Barrel 32D (° C.) | 190 | 190 | 190 | 190 | 193 | 192 | 190 | 190 |
| Temperature of Barrel 32E (° C.) | 178 | 179 | 180 | 181 | 182 | 182 | 177 | 177 |
| Temperature of Barrel 32F (° C.) | 172 | 176 | 170 | 173 | 170 | 170 | 170 | 170 |
| Temperature of Barrel 32G (° C.) | 168 | 170 | 170 | 169 | 170 | 170 | 170 | 170 |
| Temperature of Barrel 32H (° C.) | 164 | 170 | 170 | 169 | 170 | 170 | 170 | 170 |
| Temperature of Die Head (° C.) | 190 | 190 | 190 | 190 | 190 | 190 | 190 | 190 |
| Pressure of Chamber At Discharge (lb/in²) | 202 | 210 | 215 | 198 | 202 | 215 | 207 | 217 |

| | Sample # | | | | | | |
|---|---|---|---|---|---|---|---|
| | 17 | 18 | 19 | 20 | 21 | 22 | 23 |
| Rotations/Minute Of Screws | 80 | 80 | 80 | 80 | 80 | 80 | 80 |
| Input Rate Of Polymer (lb/hr) | 7.5 | 7.5 | 7.5 | 7.5 | 7.5 | 7.5 | 7.5 |
| Torque Of Screws | N/A | 79 | 76 | 68 | 75 | 66 | 75 |
| Work On Material (kW) | N/A | 1.11 | 1.07 | 0.96 | 1.06 | 0.93 | 1.06 |
| EVAL Resin lot ID | 3 | 3 | 3 | 3 | 2 | 2 | 1 |
| Fluid | ETOH | ETOH | DMSO | DMSO | DMSO | DMSO | DMSO |
| Injection Rate of Fluid (Barrel 32F) (ml/br) | 558 | 650 | 0 | 680 | 0 | 680 | 0 |
| Injection Rate of Fluid (Barrel 32G) (ml/hr) | 558 | 550 | 540 | 540 | 550 | 550 | 550 |
| Number of Injections During Process | 1 | 2 | 1 | 2 | 1 | 2 | 1 |
| Vacuum Pressure (Barrel 32F) (mm Hg) | 7.0 | 7.0 | 6.0 | 7.0 | 6.0 | 8.5 | N/A |
| Vacuum Pressure (Barrel 32G) (mm Hg) | 7.5 | 7.5 | 4.5 | 6.5 | 7.5 | 9.0 | N/A |
| Temperature of Barrel 32C (° C.) | 190 | 190 | 190 | 190 | 190 | 190 | 190 |
| Temperature of Barrel 32D (° C.) | 190 | 190 | 190 | 190 | 190 | 190 | 190 |
| Temperature of Barrel 32E (° C.) | 180 | 180 | 180 | 180 | 180 | 180 | 180 |
| Temperature of Barrel 32F (° C.) | 170 | 170 | 169 | 172 | 171 | 171 | 171 |
| Temperature of Barrel 32G (° C.) | 170 | 170 | 170 | 170 | 170 | 170 | 170 |
| Temperature of Barrel 32H (° C.) | 170 | 170 | 169 | 170 | 170 | 170 | 170 |
| Temperature of Die Head (° C.) | 190 | 190 | 190 | 190 | 190 | 190 | 190 |
| Pressure of Chamber At Discharge (lb/in²) | 197 | 216 | 210 | 215 | 207 | 147 | 157 |

| | Sample # | | |
|---|---|---|---|
| | 24 | 25 | 26 |
| Rotations/Minute Of Screws | 80 | 80 | 80 |
| Input Rate Of Polymer (lb/hr) | 7.5 | 7.5 | 7.5 |
| Torque Of Screws | 67 | 72 | 66 |

TABLE 3-continued

| | Run Conditions | | |
|---|---|---|---|
| Work On Material (kW) | 0.94 | 1.01 | 0.93 |
| EVAL Resin lot ID | 1 | 1 | 1 |
| Fluid | DMSO | DMSO | DMSO |
| Injection Rate of Fluid (Barrel 32F) (ml/hr) | 580 | 0 | 0 |
| Injection Rate of Fluid (Barrel 32G) (ml/hr) | 550 | 283 | 540 |
| Number of Injections During Process | 2 | 1 | 1 |
| Vacuum Pressure (Barrel 32F) (mm Hg) | 8.0 | Ambient | Ambient |
| Vacuum Pressure (Barrel 32G) (mm Hg) | 8.5 | Ambient | Ambient |
| Temperature of Barrel 32C (° C.) | 190 | 190 | 190 |
| Temperature of Barrel 32D (° C.) | 190 | 190 | 190 |
| Temperature of Barrel 32E (° C.) | 180 | 180 | 180 |
| Temperature of Barrel 32F (° C.) | 171 | 171 | 171 |
| Temperature of Barrel 32G (° C.) | 170 | 170 | 170 |
| Temperature of Barrel 32H (° C.) | 170 | 170 | 170 |
| Temperature of Die Head (° C.) | 190 | 190 | 190 |
| Pressure of Chamber At Discharge (lb/in²) | 134 | 120 | 75 |

It was observed that the visual appearance of the purified EVAL was significantly improved. In particular, much of the discoloration of the EVAL resin was removed by the process. Additionally, the purified EVAL resin was produced in less than four hours, significantly faster than other methods of purification.

Example 2

Some embodiments of the present invention are illustrated by the following prophetic Example. The Example is being given by way of illustration only and not by way of limitation. The example illustrates a method of making a composition for use in manufacturing a drug-eluting and/or delivery implantable medical device. The parameters and data are not be construed to unduly limit the scope of the embodiments of the invention.

The system used for this Example is similar to that illustrated in FIG. 4, and includes a gravimetric loss-in-weight feeder for feeding the polymer resin, a gravimetric loss-in-weight feeder for feeding the active agent powder and a piston pump for injecting pure solvent. The total processing barrel length may be L/D=28. Each barrel may be equipped with its own independent heating and cooling system.

As illustrated in FIG. 4, purified polymer pellets may be introduced at a feed throat at first barrel 74A of the extruder. Nitrogen may be bled at first barrel 74A to minimize the degradation of the melted polymer resin. The feed throat may be water-cooled. The polymer resin may then be heated in second barrel 74B, and melted and homogenized in third, fourth, and fifth barrels 74C, 74D, and 74E. A vacuum pump may be connected to barrel 74D for removal of some impurities from the polymer.

The pure solvent may be injected into sixth barrel 74F with a calibrated piston pump. The polymer mixture may be pressurized in seventh barrel 74G and discharged through a die plate of die head 114 at a 45 degree angle to injection molder 118.

The screw configuration for the Example is illustrated in FIG. 3. The extruder's screw configuration may be designed to provide sufficient shear rate and stress to melt the polymer pellets. The screw configuration may be similar to that described in Example 1. Table 2 provides a summary of the screw configuration. The "Element" column refers to segments of first screw 18 as illustrated in FIG. 3. Elements 13 and 20 may correspond to the segments in which the solvent may be injected into the extruder.

The "Pitch" column refers to the ratio of width/length of first screw 18 expressed in millimeters. The width is the distance between the threads of first screw 18 and the length is the length of the corresponding segment.

Table 4 provides several combinations of flow rates of polymer, solvent, and active agent. The temperatures within the extruder depend on the type of polymer.

TABLE 4

Representative flow rates of polymer, solvent, and active agent in an extruder.

| Polymer (gm/min) | Solvent (gm/min) | Active Agent (gm/min) |
|---|---|---|
| 4 | Up to 200 | 0.8 |
| 8 | Up to 400 | 1.6 |
| 4 | Up to 200 | 1.3 |
| 8 | Up to 400 | 2.6 |

While particular embodiments of the present invention have been shown and described, it will be obvious to those skilled in the art that changes and modifications can be made without departing from this invention in its broader aspects. Therefore, the appended claims are to encompass within their scope all such changes and modifications as fall within the true spirit and scope of this invention.

What is claimed is:

1. A method of making a composition for use in manufacturing an implantable medical device, comprising:
   introducing a polymer into a first segment of an extruder of a mixing apparatus allowing the polymer to flow out of an outlet of the extruder;
   introducing an active agent into a second segment of the extruder, the second segment located between the first segment and the outlet;
   removing impurities from the polymer while the polymer is in the apparatus;
   mixing the active agent with the polymer in the apparatus to form a polymer mixture;
   preventing degradation of at least some of the active agent, including controlling a temperature of the polymer mixture in at least a portion of the apparatus, wherein controlling the temperature is performed at least by either one or both of:
   (1) cooling a solvent, without the active agent, to a temperature below an ambient room temperature followed by introducing the cooled solvent, without the active agent, into the extruder, and
   (2) cooling a mixture of the solvent and the active agent to a temperature below an ambient room temperature followed by introducing the cooled mixture of the solvent and the active agent into the extruder; and
   removing the polymer mixture from the apparatus, wherein the polymer mixture is for use as a coating for an implantable medical device, or fabricating an implantable medical device.

2. The method of claim 1, further comprising coating an implantable medical device with the polymer mixture, or fabricating an implantable medical device with the polymer mixture.

3. The method of claim 1, further comprising purifying the polymer prior to mixing the polymer with the active agent and the solvent.

4. The method of claim 1, wherein the polymer mixture is homogeneous or substantially homogeneous in at least a portion of the apparatus.

5. The method of claim 1, wherein the extruder is selected from the group consisting of a single screw extruder, an intermeshing co-rotating extruder, and a counter-rotating twin extruder.

6. The method of claim 1, further comprising mixing of the polymer with the solvent and the active agent in an inert or substantially inert atmosphere.

7. The method of claim 1, further comprising heating the polymer prior to the introduction of the polymer into the apparatus.

8. The method of claim 1, further comprising heating the polymer subsequent to the introduction of the polymer into the apparatus.

9. The method of claim 1, wherein the active agent and solvent are introduced contemporaneously as a mixture, and wherein the active agent and the solvent are mixed contemporaneously with the polymer.

10. The method of claim 9, wherein the introduction of the solvent-active agent mixture is controlled to obtain a desired active agent to polymer ratio in at least a portion of the apparatus, the ratio being in the range of about 1:3 to about 1:5.

11. The method of claim 9, wherein the introduction of the solvent-active agent mixture is controlled to obtain a desired viscosity of the polymer, the viscosity being no greater than about 20,000 poises at 1 atm.

12. The method of claim 1, wherein the active agent is introduced in a solid state.

13. The method of claim 12, wherein the introduction of the solid is controlled to obtain a desired active agent to polymer ratio in at least a portion of the apparatus, the ratio being in the range of about 1:3 to about 1:5.

14. The method of claim 1, wherein the introduction of the solvent is controlled to obtain a desired active agent to polymer ratio, the ratio being in the range of about 1:3 to about 1:5.

15. The method of claim 1, wherein the introduction of the solvent is controlled to obtain a desired viscosity of the polymer, the viscosity being no greater than about 20,000 poises at 1 atm.

16. The method of claim 1, wherein controlling the temperature of the polymer mixture comprises controlling the rate of introduction of the solvent into the extruder to achieve a desired temperature range of the polymer mixture in at least a portion of the apparatus.

17. The method of claim 1, wherein the active agent and solvent are introduced contemporaneously as a mixture, and wherein controlling the temperature of the polymer mixture comprises controlling the rate of introduction of the solvent-active agent mixture into the extruder to achieve a desired temperature range of the polymer mixture in at least a portion of the apparatus.

18. The method of claim 1, wherein the temperature of the polymer mixture is controlled to be below a degradation temperature of the active agent.

19. The method of claim 1, wherein the temperature of the polymer mixture is controlled with a heat exchanger in the apparatus.

20. The method of claim 1, wherein a residence time of the polymer mixture in the apparatus is less than a time that causes a minimum acceptable degradation of the active agent.

21. The method of claim 1, wherein a residence time of the polymer mixture in the apparatus is less than about 10 seconds.

22. The method of claim 1, further comprising removing at least a portion of the solvent from the polymer mixture in the apparatus prior to removal of the polymer mixture from the apparatus.

23. The method of claim 22, wherein removing at least a portion of the solvent from the polymer mixture comprises heating at least a portion of the polymer mixture in the apparatus and extracting solvent vapor from the apparatus.

24. The method of claim 2, wherein coating the implantable medical device with the polymer mixture comprises feeding the removed polymer mixture to an injection molding apparatus and forming a coating on the implantable medical device.

25. The method of claim 2, wherein coating the implantable medical device with the polymer mixture comprises spraying the polymer mixture onto the implantable medical device.

26. The method of claim 2, wherein fabricating the implantable medical device with the polymer mixture comprises feeding the removed polymer mixture to an injection molding apparatus, and forming a tube.

27. The method of claim 26, further comprising forming a pattern comprising a network of struts on the surface of the tube.

28. The method of claim 26, further comprising disposing the tube over an uncoated implantable medical device.

29. The method of claim 1, wherein the polymer is selected from the group consisting of an ethylene vinyl alcohol copolymer, poly(butyl methacrylate), poly(vinylidene fluoride-co-hexafluororpropene), polyvinylidene fluoride, poly(L-lactic acid), poly(caprolactone), an ethylene-vinyl acetate copolymer and polyethylene glycol.

30. The method of claim 1, wherein the solvent is selected from the group consisting of water, isopropyl alcohol, methanol, flux remover, acetone, ethanol, dimethyl acetamide, acetonitrile, dimethyl formamide, cyclohexane, dimethyl sulfoxide, and combinations thereof.

31. The method of claim 1, wherein removing the impurities includes extracting the solvent from a segment of the extruder located between the second segment and the outlet of the extruder.

32. The method of claim 1, wherein removing the impurities includes extracting the solvent from a segment of the extruder located between the first segment and the second segment.

33. The method of claim 1, wherein removing the impurities includes extracting the solvent from a segment of the extruder that is located between the second segment and the outlet of the extruder and from a segment of the extruder that is located between the first segment and the second segment.

34. The method of claim 1, wherein removing the impurities includes extracting a vapor of the solvent, the vapor extraction performed using a vacuum pump attached the extruder at a segment located between the first segment and the second segment or between the second segment and the outlet of the extruder.

35. The method of claim 1, further comprising allowing the polymer mixture in the apparatus to increase in temperature above the degradation temperature of the active agent, and preventing the degradation of the active agent includes limiting residence time of the active agent in the extruder to less than about 10 seconds.

36. The method of claim 1, wherein the solvent has an ambient pressure boiling point that is below the degradation temperature of the active agent.

37. The method of claim 1, wherein the mixing of the active agent with the polymer in the apparatus to form a polymer mixture results in a homogenous or substantially homogenous mixture at the molecular- or ionic-size level of the polymer, the active agent, and the solvent.

38. The method of claim 1, wherein the segments of the extruder form a chamber configured so that the volume of the chamber is in proportion to the volume of material introduced into the segments.

39. The method of claim 1, wherein preventing the degradation of the active agent further includes introducing an inert gas in the first segment and removing atmospheric oxygen from the apparatus.

40. A method of making a composition for use in manufacturing an implantable medical device, comprising:
introducing a polymer into a first segment of an extruder;
allowing the polymer to flow out of a die of the extruder;
introducing an active agent into a second segment of the extruder, the second segment located between the first segment and the die;
mixing the active agent with the polymer in the extruder to form a polymer mixture;
controlling the temperature of the polymer mixture in at least a portion of the extruder by introducing a solvent into the extruder, wherein controlling the temperature includes varying the temperature of the solvent being introduced into the extruder;
and
removing the polymer mixture from the apparatus, wherein the polymer mixture is for use as a coating for an implantable medical device or is for fabricating an implantable medical device.

41. The method of claim 40, wherein controlling the temperature includes varying the flow rate of the solvent into the extruder.

42. The method of claim 40, wherein the solvent is introduced into the extruder as a mixture of the solvent and the active agent.

43. The method of claim 40, further comprising removing impurities from the polymer by extracting from the extruder a vapor of the solvent.

44. The method of claim 43, wherein the extraction is performed at a segment of the extruder located between the second segment and the die and at a segment of the extruder located between the first segment and the second segment.

45. A method of making a composition for use in manufacturing an implantable medical device, comprising:
introducing a polymer into a first segment of an extruder;
allowing the polymer to flow out of a die of the extruder;
introducing an active agent into a second segment of the extruder, the second segment located between the first segment and the die;
mixing the active agent with the polymer in the extruder to form a polymer mixture;
controlling the temperature of the polymer mixture in at least a portion of the extruder by introducing a solvent into the extruder;
and
removing the polymer mixture from the apparatus, wherein the polymer mixture is for use as a coating for an implantable medical device or is for fabricating an implantable medical device.

\* \* \* \* \*